(12) United States Patent
Farmer et al.

(10) Patent No.: US 11,172,669 B2
(45) Date of Patent: Nov. 16, 2021

(54) MATERIALS AND METHODS FOR THE CONTROL OF NEMATODES

(71) Applicant: LOCUS AGRICULTURE IP COMPANY, LLC, Solon, OH (US)

(72) Inventors: Sean Farmer, North Miami Beach, FL (US); Paul S. Zorner, Encinitas, CA (US); Ken Alibek, Solon, OH (US); Maja Milovanovic, North Royalton, OH (US); Sharmistha Mazumder, Copley, OH (US); Tyler Dixon, Kent, OH (US); Alex Fotsch, San Diego, CA (US)

(73) Assignee: LOCUS AGRICULTURE IP COMPANY, LLC, Solon, OH (US)

( * ) Notice: Subject to any disclaimer, the term of this patent is extended or adjusted under 35 U.S.C. 154(b) by 0 days.

(21) Appl. No.: 16/349,796

(22) PCT Filed: Nov. 16, 2017

(86) PCT No.: PCT/US2017/062056
§ 371 (c)(1),
(2) Date: May 14, 2019

(87) PCT Pub. No.: WO2018/094075
PCT Pub. Date: May 24, 2018

(65) Prior Publication Data
US 2019/0357542 A1    Nov. 28, 2019

Related U.S. Application Data

(60) Provisional application No. 62/422,918, filed on Nov. 16, 2016.

(51) Int. Cl.
| | | |
|---|---|---|
| A01N 63/32 | (2020.01) | |
| C12P 19/44 | (2006.01) | |
| A01M 17/00 | (2006.01) | |
| A01N 63/30 | (2020.01) | |

(52) U.S. Cl.
CPC ............ *A01M 17/00* (2013.01); *A01N 63/30* (2020.01); *A01N 63/32* (2020.01); *C12P 19/44* (2013.01)

(58) Field of Classification Search
CPC .................................................. A01M 17/00
See application file for complete search history.

(56) References Cited

U.S. PATENT DOCUMENTS

| | | | |
|---|---|---|---|
| 5,296,369 A | 3/1994 | Mortensen et al. | |
| 8,454,983 B2 | 6/2013 | DeChant et al. | |
| 8,975,213 B2 * | 3/2015 | Levy ..................... | A01N 63/30 504/100 |
| 9,161,545 B2 | 10/2015 | Levy et al. | |
| 2004/0115171 A1 | 6/2004 | Droby | |
| 2010/0254957 A1 | 10/2010 | Hua | |
| 2011/0044972 A1 | 2/2011 | Fieldhouse et al. | |
| 2011/0237531 A1 | 9/2011 | Yanagisawa et al. | |
| 2011/0274673 A1 | 11/2011 | Kang et al. | |
| 2012/0220464 A1 | 8/2012 | Giessler-Blank et al. | |
| 2013/0085067 A1 | 4/2013 | Schofield et al. | |
| 2013/0324406 A1 | 12/2013 | Chisholm et al. | |
| 2015/0037302 A1 | 2/2015 | Bralkowski et al. | |
| 2016/0073642 A1 | 3/2016 | Ceballos Rojas et al. | |
| 2016/0083757 A1 | 3/2016 | Fonseca et al. | |
| 2016/0152525 A1 | 6/2016 | Chelle et al. | |
| 2018/0272396 A1 * | 9/2018 | Farmer .................. | A01N 63/10 |
| 2019/0218499 A1 * | 7/2019 | Farmer .................. | C12M 23/44 |

FOREIGN PATENT DOCUMENTS

| | | |
|---|---|---|
| CN | 102613252 A | 8/2012 |
| JP | 2008501039 A | 1/2008 |
| JP | 2009126820 A | 6/2009 |
| JP | 2010200695 A | 9/2010 |
| JP | 2012176906 A | 9/2012 |
| JP | 2013017413 A | 1/2013 |
| JP | 5724089 B2 | 5/2015 |
| WO | 8103338 A1 | 11/1981 |
| WO | 9525163 A1 | 9/1995 |
| WO | 9716974 A1 | 5/1997 |
| WO | 2004020647 A1 | 3/2004 |
| WO | 2005117929 A1 | 12/2005 |
| WO | 2010012031 A1 | 2/2010 |
| WO | 2014043058 A1 | 3/2014 |
| WO | 2015089183 A2 | 6/2015 |

OTHER PUBLICATIONS

Arutchelvi et al. (Mannosylerythritol lipids: A review). (Year: 2008).*
De Almeida, D., et al., "Biosurfactants: Promising Molecules for Petroleum Biotechnology Advances." Frontiers in Microbiology, Oct. 2016, 7(1718): 1-14.
De Brito, D., Biosurfactants from renewable raw materials, Universidade do Minho Departamento de Engenharia Biologica, Portugal, Nov. 2013, pp. 1-73.
De Oliveira, M., et al., "Review: Sophorolipids A Promising Biosurfactant and it's Applications." International Journal of Advanced Biotechnology and Research, 2015, 6(2): 161-174.
Hussein, W., et al., "Systemic Resistance Induction of Tomato Plants against ToMV Virus by Surfactin Produced from Bacillus subtilis BMG02." American Journal of Microbiological Research, 2016, 4(5): 153-158.
Lee, G., et al., "Foliar application of the leafcolonizing yeast Pseudozyma churashimaensis elicits systemic defense of pepper against bacterial and viral pathogens." Scientific Reports, Jan. 2017, 7(39432): 1-13.
Sen, R., "Biosurfactants: Advances in Experimental Medicine and Biology." Landes Bioscience and Springer Science+Business Media, LLC, 2010, 672: 1-331.

(Continued)

*Primary Examiner* — Sarah Alawadi
(74) *Attorney, Agent, or Firm* — Saliwanchik, Lloyd & Eisenschenk

(57) ABSTRACT

The invention provides materials and method for controlling pests, in particular, nematodes. The invention also provides compositions comprising biosurfactants as pesticides.

8 Claims, 10 Drawing Sheets

(56) References Cited

OTHER PUBLICATIONS

Sharma, A. et al., "A study on biosurfactant production in Lactobacillus and *Bacillus* sp." Int. J. Gurr. Microbiol. App. Sci., 2014, 3(11): 723-733.

Silva, R., et al., "Applications of Biosurfactants in the Petroleum Industry and the Remediation of Oil Spills." International Journal of Molecular Sciences, 2014, 15: 12523-12542.

Takahashi, M., et al., "Production of Sophorolipid Glycolipid Biosurfactants from Sugarcane Molasses Using Starmerella bombicola NBRC 10243." Journal of Oleo Science, 2011, 60(5): 267-2733.

Rau, U., et al., "Formation and analysis of mannosylerythritol lipids secreted by Pseudozyma aphidis." Appl. Microbiol. Biotechnol., 2005, 66: 551-559.

Fan, L., et al., "Advance in glycolipid biosurfactants-mannosylerythritol lipids." Chinese Journal of Biotechnology, Sep. 25, 2013, 29(9): 1223-1233.

Morita, T., et al., "Efficient Production of Di- and Tri-acylated Mannosylerythritol Lipids as Glycolipid Biosurfactants by Pseudozyma parantarctica JCM 11752." Journal of Oleo Science, 2008, 57(10): 557-565.

\* cited by examiner

MATERIALS AND METHODS FOR THE CONTROL OF NEMATODES

CROSS-REFERENCE TO A RELATED APPLICATION

This application is a National Stage Application of International Application No. PCT/US2017/062056, filed Nov. 16, 2017; which claims the benefit of U.S. provisional application Ser. No. 62/422,918, filed Nov. 16, 2016, both of which are incorporated herein by reference in their entirety.

BACKGROUND OF INVENTION

In order to boost yields and protect crops against pathogens, pests, and disease, farmers have relied heavily on the use of synthetic chemicals and chemical fertilizers; however, when overused or improperly applied, these substances can run off into surface water, leach into groundwater, and evaporate into the air. As sources of air and water pollution, these substances are increasingly scrutinized, making their responsible use an ecological and commercial imperative. Even when properly used, the over-dependence and long-term use of certain chemical fertilizers and pesticides can deleteriously alter soil ecosystem, reduce stress tolerance, increase pest resistance, and impede plant and animal growth and vitality.

Nematodes are a class of roundworms or threadworms of the phylum Nemtoda. Examples in the class are the cyst forming nematodes of the genus *Heterodera* (e.g., *H. glycines, H. avenae*, and *H. shachtii*) and *Globodera* (e.g., *G. rostochiens* and *G. pallida*), the stubby root nematodes of the genus *Trichodorus*, the bulb and stem nematodes of the genus *Ditylenchus*, the golden nematode, *Heterodera rostochiensis*, the root knot nematodes, of the genus *Meloidogyne* (e.g., *M. javanica, M. hapla, M. arenaria* and *M. incognita*), the root lesion nematodes of the genus *Pratylenchus* (e.g., *P. goodeyi, P. penetrans, P. bractrvurus, P. zeae, P. coffeae, P. bractrvurus*, and *P. thornei*), the citrus nematodes of the genus *Tylenchulus*, and the sting nematodes of the genus *Belonalaimus*.

Nematodes are known to infect both plants and animals. These microscopic worms can be found in almost every type of environment. When residing in soil, nematodes feed on the roots of the plant, causing significant damage to the root structure and improper development of plants. The damage is generally manifested by the growth of galls, root knots, and other abnormalities. Gall formation leads to reduced root size and ineffectiveness of the root system, which, in turn, seriously affects other parts of the plant. As a result, the weakened plant becomes vulnerable to attacks by other pathogens. Without proper treatment, the plant dies. Nematodes cause millions of dollars of damage each year to turf grasses, ornamental plants, and food crops.

Root-knot nematodes (*Meloidogyne* spp.) are one of the three most economically damaging genera of plant-parasitic nematodes on horticultural and field crops. Root-knot nematodes are distributed worldwide, and are obligate parasites of the roots of thousands of plant species, including monocotyledonous and dicotyledonous, herbaceous and woody plants. Vegetable crops grown in warm climates can experience severe losses from root-knot nematodes, and are often routinely treated with a chemical nematicide. Root-knot nematode damage results in poor growth, a decline in quality and yield of the crop and reduced resistance to other stresses (e.g., drought, other diseases). A high level of damage can lead to total crop loss. For example, approximately $1.5 billion per year is lost to soybean cyst nematodes alone.

Conventional nematicides used to control nematodes are applied in the seed furrow at planting. Because of toxicity toward nearby animals, such as birds, overhead center pivots with liquid applications of toxic compounds such as Nemacur, Temik, Furadan, Dazinat and Mocap have all fallen out of favor.

Since the 1960's, methyl bromide has been used by growers to effectively sterilize fields before planting, primarily to control nematodes, as well as to treat disease and weeds; however, because this toxic compound is used in gas form, more than half the amount injected into soil can eventually end up in the atmosphere and contribute to the thinning of the ozone layer. In 2005, developed countries banned methyl bromide under the Montreal Protocol, which is an international treaty signed in 1987 to protect the stratospheric ozone layer.

Under the ban, the treaty allows limited use of methyl bromide in strawberries, almonds, and other crops that lack alternatives for both effective and affordable control of nematodes, disease, and weeds. The extent of authorized use diminishes every year and will likely end soon. Finding alternatives to methyl bromide is, thus, a priority for growers and regulatory agencies; however, no single product provides the wide spectrum of control offered by methyl bromides.

Mounting regulatory mandates governing the availability and use of chemicals, as well as consumer demands for residue free, sustainably-grown food are impacting the industry and causing an evolution of thought regarding how to address the myriad of challenges. While wholesale elimination of chemicals is not feasible at this time, farmers are increasingly embracing the use of biological measures as viable components of Integrated Nutrient Management and Integrated Pest Management programs.

Due to the disadvantages of the major approaches described above, the demand for safer pesticides and alternate pest control strategies is increasing. Particularly, in recent years, biological control of nematodes has caught great interest. This method utilizes biological agents such as live microbes, bio-products derived from these microbes, and combinations thereof as pesticides. These biological pesticides have important advantages over other conventional pesticides. For example, they are less harmful compared to the conventional chemical pesticides. They are more efficient and specific, and they often biodegrade quickly, leading to less environmental pollution.

The use of biopesticides and other biological agents has been greatly limited by difficulties in production, transportation, administration, pricing and efficacy. For example, many microbes are difficult to grow and subsequently deploy to agricultural and forestry production systems in sufficient quantities to be useful. This problem is exacerbated by loses in viability and/or activity due to processing, formulating, storage, stabilizing prior to distribution, sporulation of vegetative cells as a means of stabilizing, transportation, and application. Furthermore, once applied, biological products may not thrive for any number of reasons including, for example, insufficient initial cell densities, the inability to compete effectively with the existing microflora at a particular location, and being introduced to soil and/or other environmental conditions in which the microbe cannot flourish or even survive.

Therefore, there is an urgent need for development of methods and materials for producing effective biopesticides to control nematodes.

BRIEF SUMMARY

The subject invention provides compositions and methods for controlling nematodes. In addition, the subject invention provides methods and compositions for preventing damage to crops from nematodes, thus resulting in yield increase. Advantageously, the pesticides according to the subject invention utilize non-toxic substances, such as microbes and by-products of microbial cultivation.

In one embodiment, the subject invention provides methods for preventing nematode damage and controlling nematodes, comprising the steps of: cultivating a microorganism that produces a microbial growth by-product and contacting the nematodes, or their environment, with an effective amount of the microbe and/or the microbial growth by-product.

In one embodiment, the microbial growth by-product is a biosurfactant. In one embodiment, the biosurfactant is a glycolipid such as a rhamnolipid, sophorolipid (SLP), trehalose lipid or mannosylerythrithol lipid (MEL). In particularly preferred embodiments the biosurfactant is an SLP and/or MEL.

The microbe-based nematicidal compositions of the subject invention can be obtained through cultivation processes ranging from small to large scale. These cultivation processes include, but are not limited to, submerged cultivation/fermentation, surface cultivation, solid state fermentation (SSF), and combinations thereof. The nematicidal composition may be, for example, the fermentation broth and/or purified biosurfactants.

In some embodiments, the biosurfactant-producing microorganisms in the composition can be grown onsite and produce the biosurfactants for direct use to control nematodes. Consequently, a high concentration of biosurfactant and/or biosurfactant-producing microorganisms at a treatment site (e.g., soil) can be achieved easily and continuously.

In one embodiment, the system according to the subject invention comprises an additional aspect providing for field application of the microbe-based products. The microbe-based products of the subject invention may be applied, for example, through an irrigation system, as a spray, as a seed treatment, to the soil surface, to plant surfaces, and/or to pest surfaces. Mechanical application through conventional implements or robotic application through aerial or ground based "drones" is also facilitated.

The nematicidal composition may be used to protect plants, humans, or animals by controlling nematodes.

DETAILED DISCLOSURE

Figure 1:
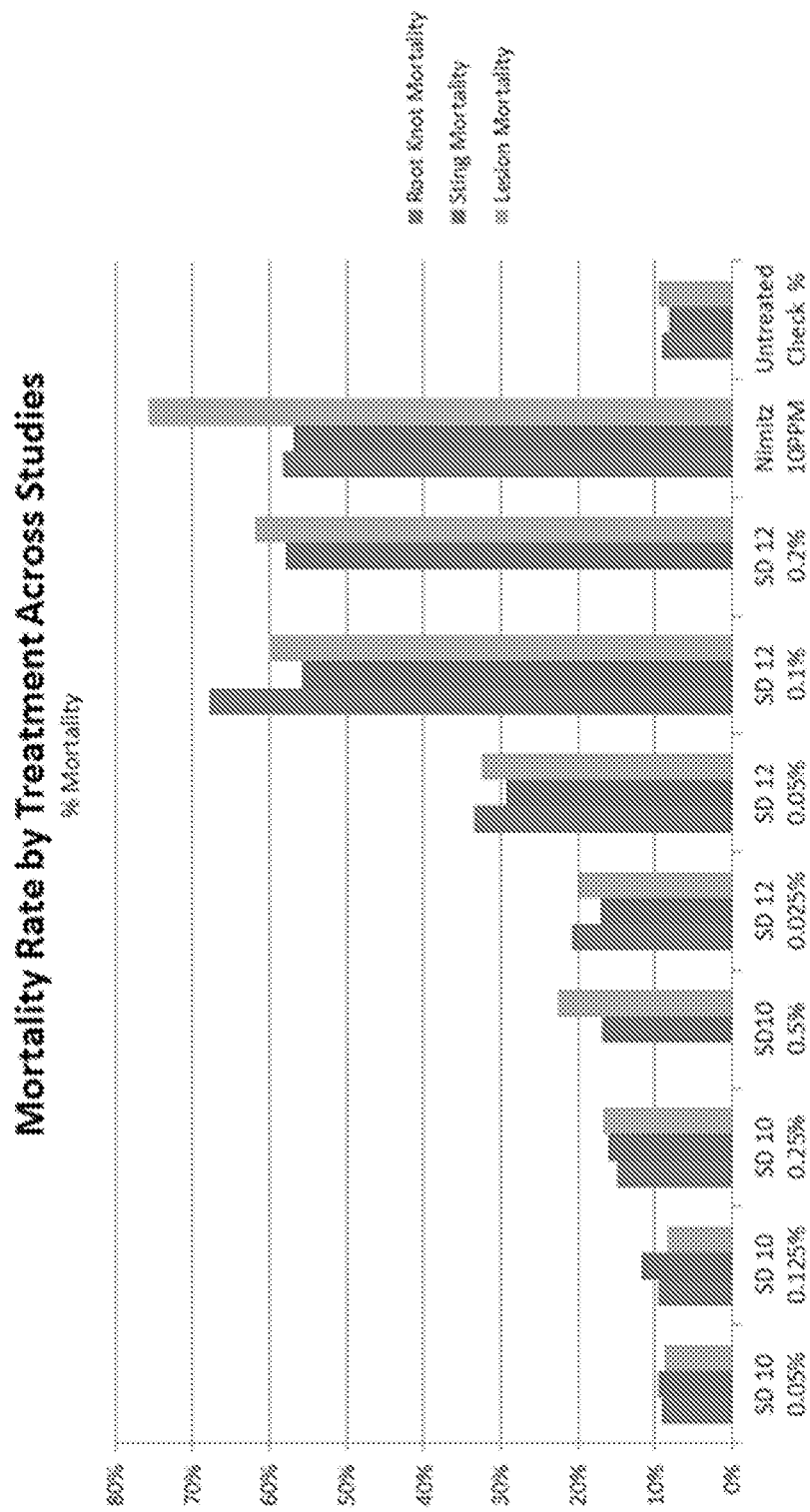
FIG. 1 shows nematode motility reduction after 3 days of treatment under various conditions: SD10 at 0.05% (v/v), 0.125% (v/v), 0.25% (v/v), and 0.5% (v/v), respectively; SD12 at 0.025% (v/v), 0.05% (v/v), 0.1% (v/v), and 0.2% (v/v), respectively; Nimitz® at 10 ppm ai; and untreated check. SD10 refers to SLP treatment. SD12 refers to MEL treatment.

The subject invention provides materials and methods for controlling nematodes. The subject invention also provides compositions that can be used as pesticides for controlling nematodes. The subject invention further provides methods for preparing such compositions. In addition, the subject invention provides methods and compositions for preventing the damage of crops from nematodes, thus resulting in yield increases.

The microbe-based products of the subject invention can be used in settings including, but not limited to, crops, livestock, forestry, turf management, pastures, and human and animal health.

In one embodiment, the composition for controlling nematodes according to the subject invention comprises an effective amount of a microbial biosurfactant and/or a microorganism producing such biosurfactant.

In one embodiment, the method of controlling nematodes comprises the steps of obtaining a microbial biosurfactant, and applying an effective amount of the microbial biosurfactant to nematodes or to their locus.

The compositions according to the subject invention can be obtained by, for example, cultivation processes ranging from small to large scales. These cultivation processes include, but are not limited to, submerged cultivation/fermentation, surface cultivation, solid state fermentation (SSF), and combination thereof.

The product of fermentation containing the microbial biosurfactant may be used directly for nematode treatments without extraction or purification. If desired, extraction and purification of the biosurfactants can be achieved as described herein. Advantageously, the cultivation method according to the invention is able to produce a high concentration of microorganisms and a high concentration of biosurfactant.

In certain embodiments, the methods and compositions according to the subject invention reduce damage caused by nematodes, compared to an untreated plant, by about 5%, 10%, 20%, 30%, 40%, 50%, 60% 70%, 80%, or 90% or more.

In one embodiment, the subject invention provides a method of increasing crop or plant yields. In certain embodiments, the methods and compositions according to the subject invention increase crop yield by about 5%, 10%, 20%, 30%, 40%, 50%, 60% 70%, 80%, or 90% or more compared to an untreated plant.

In one embodiment, the methods of the subject invention reduce the number of nematode eggs in the roots of a plant by about 5%, 10%, 20%, 30%, 40%, 50%, 60% 70%, 80%, or 90% or more compared to an untreated plant.

In another embodiment, the subject invention provides a method of increasing plant weight or size relative to an untreated plant.

Selected Definitions

As used herein, the term "control" used in reference to the activity produced by the biosurfactants or biosurfactant-producing microorganisms extends to the act of killing, disabling or immobilizing pests or otherwise rendering the pests substantially incapable of causing harm.

As used herein "nematicidal" means having the ability to control nematodes. Thus, for example, killing nematodes, reducing their motility, and reducing egg counts are all examples of nematicidal activity.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with broth in which they were grown, in the microbe-based composition. The cells may be present at, for example, a concentration of $1\times10^4$, $1\times10^5$, $1\times10^6$, $1\times10^7$, $1\times10^8$, $1\times10^9$, $1\times10^{10}$, or $1\times10^{11}$ or more propagules per milliliter of the composition. As used herein, a propagule is any portion of a microorganism from which a new and/or mature organism can develop, including but not limited to, cells, spores, mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

Microorganisms

Microbial biosurfactants are compounds produced by a variety of microorganisms such as bacteria, fungi, and yeasts.

In one embodiment, the microorganisms are bacteria including gram-positive and gram-negative bacteria. These bacteria may include, but are not limited to, for example, *Escherichia coli*, *Rhizobium* (e.g. *Rhizobium japonicum*, *Sinorhizohizoum meliloti*, *Sinorhizobium fredii*, *Rhizobium leguminosarum biovar trifblii*, and *Rhizobium etli*), *Bradyrhizobium* (e.g. *B. japanicum*, and *B. parasponia*), *Bacillus* (e.g. *B. subtilis*, *B. firmus*, *B. laterosporus*, *B. pumillus*, *B. cereus*, *B. licheniformis*, *B. megaterium*, and *B. amyloliquifaciens*), *Azobacter* (e.g. *A. vinelandii*, and *A. chroococcum*), *Arthrobacter* (e.g. *A. pascens*), *Agrobacterium* (e.g., *A. radiobacter*), *Pseudomonas* (e.g. *P. chlororaphis* subsp. *aureofaciens* (*Kluyver*), *P. aeruginosa*, *P. putida*, *P. florescens*, *P. fragi*, and *P. syringae*), *Flavobacterium* spp.; *Azospirillium* (e.g. *A. brasiliensis*), *Azomonas*, *Derxia*, *Beijerinckia*, *Nocardia*, *Klebsiella*, *Clavibacter* (e.g. *C. xyli* subsp. *xyli* and *C. xyli* subsp. *cynodontis*), *Cyanobacteria*, *Pantoea* (e.g. *P. agglomerans*), *Sphingomonas* (e.g. *S. paucimobilis*), *Streptomyces* (e.g. *S. griseochromogenes*, *S. qriseus*, *S. cacaoi*, *S. aureus*, and *S. kasugaenis*), *Streptoverticillium* (e.g. *S. rimofaciens*), *Ralslonia* (e.g. *R. eulropha*), *Rhodospirillum* (e.g. *R. rubrum*), *Xanthomonas* (e.g. *X. campestris*), *Erwinia* (e.g. *E. carotovora*), *Clostridium* (e.g. *C. butyricum*, *C. tyrobutyricum*, *C. acetobutyricum*, *C. beijerinckii*, *C. bravidaciens*, and *C. malacusomae*), *Rhodococcus*, *Campylobacter*, *Cornybacterium*, and combinations thereof.

In another embodiment, the microorganism is a yeast. A number of yeast species are suitable for production according to the current invention, including, but not limited to, *Saccharomyces* (e.g. *S. cerevisiae*, *S. boulardii sequela* and *S. torula*), *Debaromyces*, *Issalchenkia*, *Candida* (*C. albicans*, *C. rugosa*, *C. tropicalis*, *C. lipolytica*, and *C. torulopsis*), *Kluyveromyces* (e.g. *K. lactis*, *K. fragilis*), *Pichia* (e.g. *Pichia pastoris*), *Wickerhamomyces*, *Starmerella* (e.g., *Starmerella bombicola*), and/or combinations thereof.

In one embodiment, the yeast is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include *Fusarium* and other filamentous fungi. Examples of killer yeasts according to the present invention are those that can be used safely in the food and fermentation industries, e.g., beer, wine, and bread making; those that can be used to control other microorganisms that might contaminate such production processes; those that can be used in biocontrol for food preservation; those than can be used for treatment of fungal infections in both humans and plants; and those that can be used in recombinant DNA technology. Such yeasts can include, but are not limited to,

*Wickerhamomyces, Pichia* (e.g., *Pichia anomala, Pichia guielliermondii, Pichia kudrizvzevii*) *Hansenula, Saccharomyces, Hanseniaspora*, such as *Hanseniaspora uvarum, Ustilago maydis, Debaryomyces hansenii, Candida, Cryptococcus, Kluyveromyces, Torulopsis, Ustilago, Williopsis, Zygosaccharomyces*, such as *Zygosaccharomyces bailii*, and others.

In one embodiment, the microorganisms are fungi, including, but not limited to, *Mycorrhiza* (e.g. vesicular-arbuscular mycorrhizae (VAM), arbuscular mycorrhizae (AM)), *Mortierella, Phycomyces, Blakeslea, Thraustochytrium, Penicillium, Phythium, Entomophthora, Aureobasidium pullulans, Fusarium venenalum, Aspergillus, Trichoderma* (e.g. *T. reesei, T. harzianum, T. viride* and *T. hamatum*), *Rhizopus* spp, endophytic fungi (e.g. *Piriformis indica*) and combinations thereof.

In a further embodiment, the microorganisms are Mycorrhizal fungi such as *Glomus* spp. and *Acaulospora* spp. In one embodiment, the microorganism is arbuscular mycorrhizal fungi (AMF).

In specific embodiments, microbes for the production of SLPs can be *Candida sp., Starmerella sp., Cryptococcus sp., Cyberlindnera samutprakarnensis* JP52 (T), *Pichia sp., Rhodotorula sp.*, or *Wickerhamiella sp.*

In further specific embodiments, microbes for the production of MELs can be *Pseudozyma sp., Candida sp., Ustilago sp., Schizonella sp.*, or *Kurtzmanomyces sp.*

In preferred embodiments, the microbes are yeasts. In specific embodiments, the yeasts are *Starmerella, Pichia*, and/or *Pseudozyma*. Specifically exemplified herein are *Starmerella bombicola, Pichia anomala* (*Wickerhamomyces anomalus*) and *Pseudozyma aphidis*.

Biosurfactants

Biosurfactants form an important class of secondary metabolites that occur in many microorganisms. Biosurfactants are biodegradable and can be easily and cheaply produced using selected organisms on renewable substrates. Most biosurfactant-producing organisms produce biosurfactants in response to the presence of hydrocarbon source (e.g., oils, sugar, glycerol, etc.) in the growing media. Other media components can also affect biosurfactant production significantly. For example, the production of rhamnolipids by the bacteria *Pseudomonas aeruginosa* can be increased if nitrate is used as a source of nitrogen rather than ammonium. The concentration of iron, magnesium, sodium, and potassium; the carbon:phosphorus ratio; and agitation can greatly affect rhamnolipid production as well.

Biosurfactants include low molecular weight glycolipids (GLs), lipopeptides (LPs), flavolipids (FLs), phospholipids, and high molecular weight polymers such as lipoproteins, lipopolysaccharide-protein complexes, and polysaccharide-protein-fatty acid complexes. The common lipophilic moiety of a biosurfactant molecule is the hydrocarbon chain of a fatty acid, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

According to embodiments of this invention, the biosurfactant is able to penetrate through pests' tissues and is effective in lesser amounts without the use of adjuvants. It has been found that at concentrations above the critical micelle concentration, the biosurfactants are able to penetrate more effectively into treated objects.

The development of the natural biopesticides of the subject invention, which can be produced in high amounts, represents a significant advancement in the art. Pests can be controlled using either the biosurfactant-producing organisms as a biocontrol agent or by the biosurfactants themselves. In addition, pest control can be achieved by the use of specific substrates to support the growth of biosurfactant-producing organisms as well as to produce biosurfactant pesticidal agents. Advantageously, natural biosurfactants are able to inhibit the growth of competing organisms and enhance the growth of the specific biosurfactant producing organisms.

In addition, these biosurfactants can play important roles in treating animal and human diseases. Animals can be treated by, for example, by dipping or bathing in a biosurfactant solution alone, with or without microbe cell mass, and/or in the presence of other compounds such as copper or zinc.

Methods for Culturing the Microbes

The subject invention provides methods for cultivation of microorganisms and production of biosurfactants and/or other by-products of microbial growth. These cultivation processes include, but are not limited to, submerged cultivation/fermentation, surface cultivation, solid state fermentation (SSF), and combination thereof.

The microbial cultivation systems would typically use submerged culture fermentation; however, surface culture and hybrid systems can also be used. As used herein "fermentation" refers to growth of cells, spores, mycelia and/or other microbial propagules under controlled conditions. The growth could be aerobic or anaerobic.

The microbe growth vessel used according to the subject invention can be any fermenter or cultivation reactor for industrial use. The cultivation process is carried out in a vessel that may be, for example, conical or tubular. In one embodiment, the vessel may optionally have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of bacteria in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, canola oil, coconut oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before, and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

The biomass content of the fermentation broth may be, for example from 5 g/l to 180 g/l or more. In one embodiment, the solids content of the broth is from 10 g/l to 150 g/l.

In one embodiment, the method for producing a microbial metabolite according to the subject invention comprises the steps of: 1) mixing hydrophobic and hydrophilic particles to form a matrix-forming solid substance; 2) contacting said matrix-forming solid substance with a medium inoculated with a microorganism of interest, thereby creating a matrix of micro-reactors; and 3) growing said microorganism within said micro-reactors.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

In one embodiment, the microbes are cultivated within 100, 50, 25, 10, 5, 1, or less miles of where the microbe-based product will be used.

Preparation of Microbe-Based Products

One microbe-based product of the subject invention is simply the fermentation broth containing the microorganism and/or the microbial metabolites (such as biosurfactants) produced by the microorganism and/or any residual nutrients. The product of fermentation may be used directly without extraction, isolation, or purification. If desired, extraction, isolation and/or purification can be easily achieved using standard methods or techniques described herein and/or in the literature.

The microorganisms in the microbe-based product may be in an active or inactive form, in cell form, spore form, and/or mycelial form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or broth (including discrete layers or fractions) resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

As used herein "broth" includes the whole broth or fractions of the whole broth.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, pH modifiers, nutrients for microbe growth, nutrients for plant growth, tracking agents, pesticides, herbicides, animal feed, food products and other ingredients specific for an intended use.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored for longer periods of time and at ambient temperatures.

In one embodiment, the cultivation products may be prepared as a spray-dried biomass product. The biomass may be separated by known methods, such as centrifugation, filtration, separation, decanting, a combination of separation and decanting, ultrafiltration or microfiltration. The biomass product may be separated from the cultivation medium, and spray-dried.

The microbe-based products may be formulated in a variety of ways, including liquid, solids, granular, dust, or slow release products by means that will be understood by those of skill in the art having the benefit of the instant disclosure.

For human or animal applications, the formulations may be prepared in liquid, paste, ointment, suppository, capsule or tablet forms and used in a way similar to drugs used in the medicinal drugs industry. The formulations can be encapsulated using components known in the pharmaceutical industry. Encapsulation protects the components from undesirable reactions and helps the ingredients resist adverse conditions in the environment or the treated object or body e.g., the stomach.

Solid formulations of the invention may have different forms and shapes such as cylinders, rods, blocks, capsules, tablets, pills, pellets, strips, spikes, etc. Solid formulations may also be milled, granulated or powdered. The granulated or powdered material may be pressed into tablets or used to fill pre-manufactured gelatin capsules or shells. Semi solid formulations can be prepared in paste, wax, gel, or cream preparations.

The solid or semi-solid compositions of the invention can be coated using film-coating compounds used in the pharmaceutical industry such as polyethylene glycol, gelatin, sorbitol, gum, sugar or polyvinyl alcohol. This is particularly essential for tablets or capsules used in pesticide formulations. Film coating can protect the handler from coming in direct contact with the active ingredient in the formulations.

In addition, a bittering agent such as denatonium benzoate or quassin may also be incorporated in the pesticidal formulations, the coating or both.

The compositions of the invention can also be prepared in powder formulations and filled into pre-manufactured gelatin capsules.

The concentrations of the ingredients in the formulations and application rate of the compositions may be varied widely depending on the pest, plant or area treated, or method of application.

In preferred embodiments, the composition for controlling nematodes according to the subject invention comprises an effective amount of a microbial biosurfactant.

In one embodiment, the microbial biosurfactant is a glycolipid such as a rhamnolipid, sophorolipids (SLP), trehalose lipid and/or mannosylerythrithol lipid (MEL).

In one embodiment, the composition for controlling nematodes according to the subject invention comprises an effective amount of a single microbial biosurfactant and/or a single microorganism producing the biosurfactant. In another embodiment, the composition for controlling nematodes may comprise a mixture of microbial biosurfactants and/or a mixture of microorganisms producing these biosurfactants.

In one embodiment, the composition for controlling nematodes comprises SLP. SLP may be in a purified form or in a mixture of fermentation products. The composition preferably contains the active components, such as the SLP, at concentrations of 0.01 to 90 by weight % (wt %), preferably 0.1 to 50 wt %, and more preferably 0.1 to 20 wt %. In another embodiment, purified SLP may be in combination with an accepted carrier, in that SLP may be presented at concentrations of 0.001 to 50% (v/v), preferably, 0.01 to 20% (v/v), more preferably, 0.02 to 5% (v/v).

In one embodiment, the composition for controlling nematodes comprises MEL. MEL may be in a purified form or in a mixture of fermentation product. The composition preferably contains the active components, such as the MEL, at concentrations of 0.01 to 90 by weight % (wt %), preferably 0.1 to 50 wt %, and more preferably 0.1 to 20 wt %. In another embodiment, purified MEL may be in combination with an accepted carrier, in that MEL may be presented at concentrations of 0.0001 to 50% (v/v), preferably, 0.005 to 20% (v/v), more preferably, 0.001 to 5% (v/v).

In another embodiment, the composition for controlling nematodes comprises a mixture of SLP and MEL. SLP and MEL may be mixed at any ratio as long as the composition contains the active components, the combination of SLP and MEL, at concentration of 0.01 to 90 by weight % (wt %), preferably 0.1 to 50 wt %, and more preferably 0.1 to 20 wt %. In another embodiment, purified SLP and MEL may be in combination with an accepted carrier, in that SLP may be presented at concentrations of 0.0001 to 50% (v/v), preferably, 0.005 to 20% (v/v), more preferably, 0.001 to 5% (v/v).

In a further embodiment, the composition comprises SLP and/or MEL in combination with a strain of microorganism producing SLP and/or MEL, such as, e.g., *Starmerella, Wickerhamomyces anomalus* or *Pseudozymas* species.

The biosurfactants may be used either alone or combined with other acceptable active or inactive components. These components can be, for example, an oil component such as cinnamon oil, clove oil, cottonseed oil, garlic oil, or rosemary oil; another natural surfactant such as Yucca or Quillaja saponins; or the component may be an aldehyde such as cinnamic aldehyde. Other oils that may be used as a pesticidal component or adjuvants include: almond oil, camphor oil, canola oil, castor oil, cedar oil, citronella oil, *citrus* oil, coconut oil, corn oil, *eucalyptus* oil, fish oil, geranium oil, lecithin, lemon grass oil, linseed oil, mineral oil, mint or peppermint oil, olive oil, pine oil, rapeseed oil, safflower oil, sage oils, sesame seed oil, sweet orange oil, thyme oil, vegetable oil, and wintergreen oil.

Other acceptable components can be, for example, nematode attracting substances, such as soluble and gaseous substances produced by the roots of host plants or by attendant rhizosphere microorganisms. One example of a nematode attractant according to the subject invention is Valerian root (*Valeriana officianalis*). Particularly, solutions comprising Valerian root extract, as well as any other compound or by-product associated with Valerian plant roots, can be used as an attractant according to the subject compositions and methods.

Other suitable additives, which may be contained in the formulations according to the invention, include substances that are customarily used for such preparations. Example of such additives include adjuvants, surfactants, emulsifying agents, plant nutrients, fillers, plasticizers, lubricants, glidants, colorants, pigments, bittering agents, buffering agents, solubility controlling agents, pH adjusting agents, preservatives, stabilizers and ultra-violet light resistant agents. Stiffening or hardening agents may also be incorporated to strengthen the formulations and make them strong enough to resist pressure or force in certain applications such as soil, root flare or tree injection tablets.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as sodium bicarbonate or carbonate, sodium sulfate, sodium phosphate, sodium biphosphate, can be included in the formulation.

In one embodiment, the compositions can include one or more chemical compounds with nematicidal activity. These include antibiotic nematicides such as abamectin; carbamate nematicides such as benomyl, carbofuran, carbosulfan, and cleothocard; oxime carbamate nematicides such as alanycarb, aldicarb, aldoxycarb, oxamyl; organophosphorous nematicides such as diamidafos, fenamiphos, fosthietan, phosphamidon, cadusafos, chlorpyrifos, dichlofenthion, dimethoate, ethoprophos, fensulfothion, fosthiaZate, heterophos, isamidofos, isaZofos, methomyl, phorate, phosphocarb, terbufos, thiodicarb, thionaZin, triaZophos, imicyafos, and mecarphon. Other compounds with nematicidal activity include acetoprole, benclothiaz, chloropicrin, dazomet, DBCP, DCIP, 1,2-dichloropropane, 1,3-dichloropropene, furfural, iodomethane, metam, methyl bromide, methyl isothiocyanate, and xylenols.

In one embodiment, the compositions can further comprise an effective amount of at least one insecticide. Suitable insecticides include, but are not limited to, non-nematicidal, neonicotinoid insecticides such as 1-(6-chloro-3-pyridylmethyl)-N-nitroimidazolidin-2-ylideneamine (imidacloprid); 3-(6-chloro-3-pyridylmethyl)-1,3-thiazolidin-2-ylidenecyanamide (thiacloprid); 1-(2-chloro-1,3-thiazol-5-ylmethyl)-3-methyl-2-nitroguanidine (clothianidin); nitempyran; $N^1$-[(6-chloro-3-pyridyl)methyl]-$N^2$-cyano-$N^1$-methylacetamidine (acetamiprid); 3-(2-chloro-1,3-thiazol-5-ylmethyl)-5-methyl-1,3,5-oxadiazinan-4-ylidene(nitro) amine (thiamethoxam); and 1-methyl-2-nitro-3-(tetrahydro-3-furylmethyl)guanidine (dinotefuran).

Application of the Microbe-Based Products

In yet another aspect, the subject invention includes methods, systems, and devices for applying the microbe-based products.

In one embodiment, the subject invention provides a method of improving plant health and/or increasing crop yield by applying the composition disclosed herein to soil, seed, or plant parts. In another embodiment, the subject invention provides a method of increasing crop or plant yield comprising multiple applications of the composition described herein.

Advantageously, the method can effectively control nematodes, and the corresponding diseases caused by pests while a yield increase is achieved and side effects and additional costs are avoided.

In one embodiment, the composition can be applied to an already germinated and/or growing plant including roots, stems, and leaves. The composition may also be applied as a seed treatment. The use as a seed treatment is beneficial because the application can be achieved easily, and the amount used for treatment may be reduced, further reducing the potential toxicity, if any.

In one embodiment, biosurfactant-producing microorganisms and/or biosurfactants may be added to the soil, plants' growing medium, plants, aquatic medium, or any area to be treated to prevent pest damage. The microorganisms can grow in situ and produce the biosurfactants onsite to control nematodes. In addition, natural biosurfactant-producing organisms applied at the site of application will be able to grow and produce the biosurfactant. Consequently, a high concentration of biosurfactant and biosurfactant-producing microorganisms at treatment site (e.g., soil) can be achieved easily and continuously.

Substances that enhance the growth of microorganisms and the production of biosurfactants may also be added to the composition and/or the treatment site to support the growth of biosurfactant-producing organisms as well as to produce the desired biosurfactants on site to achieve the objective of the invention. These substances include, but are not limited to, carbon, or organic substrates such as oil, glycerol, sugar, or other nutrients. For example, biosurfactant producing organisms can grow on the substrate to produce biosurfactant in place and control nematodes. Natural biosurfactant-producing organisms at the site of application (soil, aquatic system, plant parts, etc.) will produce biosurfactants while utilizing the carbon substrate. During this process, the biosurfactant produced will destroy or paralyze pests in the targeted area. According to the invention, it is not necessary to pre-inoculate the targeted site or the carbon substrate mixture with biosurfactant-producing organisms.

Carbon substrates can include, but are not limited to, organic carbon sources such as natural or synthetic oil including used frying oil; fat; lipid; wax (natural or paraffin); fatty acids such as lauric; myristic, etc; fatty acid alcohol such as lauryl alcohol; amphiphilic esters of fatty acids with glycerol such as glyceryl monolaurate; glycol esters of fatty acid such as polyethylene monostearate; fatty acid amines such as lauryl amine; fatty acid amides; hexanes; glycerol;

glucose; etc. It is preferable to use a water insoluble carbon substrate to encourage production of the biosurfactants.

One embodiment involves spiking or amending the carbon substrate with a sufficient amount of specific biosurfactant to initiate the emulsification process and to inhibit or reduce the growth of other competing organisms for the biosurfactant-producing organism and to control nematodes. *Pseudomonas syringae* and *Bacillus subtilis*, for instance, produce a series of lipopeptides biosurfactants referred to as porens. These lipopeptide porens include pseudomycin, syringomycin, tabtoxin, phaseolotoxin, and surfactin. Some lipopeptides are capable of creating holes in cell membranes, cells, and tissues.

Pseudomycin can be applied as a pre-plant treatment for nematode control in crop production. If it is desired to encourage the growth of *Bacillus subtilis*, a small amount of surfactin biosurfactant is added to the carbon substrate medium to aid in establishment of *B. subtilis* population and the production of more surfactin on-site.

In one embodiment, the composition may be applied by spraying, pouring, dipping, in the form of concentrated or diluted liquids, solutions, suspensions, powders, and the like, containing such concentrations of the active agent as is most suited for a particular purpose at hand. They may be applied as is or reconstituted prior to use. For example, they may be applied by direct injection into trees or root flares.

In one embodiment, the composition according to the subject invention may be applied at about 0.0001 pounds/acre to about 10 pounds/acre, about 0.001 pounds/acre to about 5 pounds/acre, about 0.01 pounds/acre to about 1 pounds/acre, about 0.01 pounds/acre to about 0.1 pounds/acre, or about 0.01 pounds/acre to about 0.05 pounds/acre.

In one embodiment, the composition according to the subject invention is applied to the plant or crop from about 1 to about 100 days, about 2 to about 50 days, about 10 to about 40 days, about 20 to about 30 days after the initial application to soil or seed.

In specific embodiments, the compositions may be, for example, introduced into an irrigation system, sprayed from a backpack or similar devices, applied by a land based or airborne robotic device such as a drone, and/or applied with a seed.

Seed application may be by, for example, a seed coating or by applying the composition to the soil contemporaneously with the planting of seeds. This may be automated by, for example, providing a device or an irrigation system that applies the microbe-based composition along with, and/or adjacent to, seeds at, or near, the time of planting the seeds. Thus, the microbe-based composition can be applied within, for example, 5, 4, 3, 2, or 1 day before or after the time of plantings or simultaneously with planting of the seeds.

In certain embodiments, the compositions provided herein are applied to the soil surface without mechanical incorporation. The beneficial effect of the soil application can be activated by rainfall, sprinkler, flood, or drip irrigation, and subsequently delivered to, for example, targeted pests in order to drive their population levels down to acceptable thresholds or to the roots of plants to influence the root microbiome or facilitate uptake of the microbial product into the vascular system of the crop or plant to which the microbial product is applied. In an exemplary embodiment, the compositions provided herein can be efficiently applied via a center pivot irrigation system or with a spray over the seed furrow.

Reference herein to administration of the composition "on or near" a pest or a plant, or to the "environment" of a pest or plant, means that the administration is such that the composition is sufficiently in contact with the pest or plant such that the desired result (e.g., killing the pest, increasing yield, preventing damage to the plant, regulating genes and/or hormones, etc.) is achieved. This may typically be within, for example, 10, 5, 3, 2, or 1 feet or less, of the pest, plant, weed, or other desired target.

The microbe-based product may also be applied so as to promote colonization of the roots and/or rhizosphere as well as the vascular system of the plant in order to promote plant health and vitality. Thus, nutrient-fixing microbes such as rhizohium and/or mycorrhzae can be promoted as well as other endogenous (already present in the soil), as well as exogenous, microbes, or their by-products, that combat pests, or disease, or otherwise promote crop growth, health and/or yield. The microbe-based product can also support a plant's vascular system by, for example, entering and colonizing said vascular system and contributing metabolites, and nutrients important to plant health and productivity or metabolites with pest controlling properties.

Advantageously, the method does not require complicated equipment or high energy consumption. The microorganisms of interest can be cultivated at small or large scale on site and utilized, even being still mixed with their media. Similarly, the microbial metabolites can also be produced at large quantities at the site of need.

Advantageously, the microbe-based products can be produced in remote locations. In one embodiment, the microbe-based products can be used for human nutrition and/or disease prevention and/or treatment.

Target Pests

In preferred, but non-limiting, embodiments of the invention the nematode controlled is chosen from:

(1) a nematode that is a plant pathogenic nematode, such as but not limited to: Root Knot Nematodes (*Meloidogyne* spp.) in rice (e.g., *M. incognita, M. javanica* or *M. graminicola*), in soybean (e.g., *M. incognita* or *M. arenaria*), in cotton (e.g., *M. incognita*), in potato (e.g., *M. chitwoodi* or *M. hapla*), in tomato (e.g., *M. chitwoodi*), in tobacco (e.g., *M. incognita, M. javanica* or *M. arenaria*), and in corn (e.g., *M. incognita*); Cyst Nematodes (*Heterodera* spp.) in rice (e.g., *H. oryzae*), in soybean (e.g., *H. glycines*) and in corn (e.g., *H. zeae*); Cyst nematodes (*Globodera* spp.) in potato (e.g., *G. pallida* or *G. rostochiensis*); Reniform Nematodes (*Rotylenchulus* spp.) in cotton (e.g., *R. reniformis*); Root lesion nematodes (*Pratylenchus* spp.) in banana (e.g., *P. coffeae* or *P. goodeyi*); Burrowing Nematodes (*Radopholus* spp.) in banana (e.g., *R. similis*); and other rice damaging nematodes such as rice root nematode (*Hirschmaniella* spp., e.g. *H. oryzae*);

(2) a nematode capable of infesting humans such as, but not limited to: *Enterobius vermicularis*, the pinworm that causes enterobiasis; *Ascaris lumbridoides*, the large intestinal roundworm that causes ascariasis; *Necator* and *Ancylostoma*, two types of hookworms that cause ancylostomiasis; *Trichuris trichiura*, the whipworm that causes trichuriasis; *Strongyloides stercoralis* that causes strongyloidiasis; and *Trichonella spirae* that causes trichinosis; *Brugia malayi* and *Wuchereria bancrofti*, the filarial nematodes associated with the worm infections known as lymphatic filariasis and its gross manifestation, elephantiasis, and *Onchocerca volvulus* that causes river blindness;

(3) a nematode capable of infesting animals such as, but not limited to: dogs (Hookworms e.g., *Ancylostoma caninum* or *Uncinaria stenocephala*, Ascarids e.g., *Toxocara canis* or *Toxascaris leonina*, or Whipworms e.g., *Trichuris vulpis*), cats (Hookworms e.g., *Ancylostoma tubaeforme*, Ascarids e.g., *Toxocara cati*), fish (herring worms or cod worms e.g., Anisakid, or tapeworm e.g., *Diphyllobothrium*), sheep (Wire worms e.g., *Haemonchus contortus*) and cattle (Gastro-intestinal worms e.g., *Ostertagia ostertagi, Cooperia oncophora*);

(4) a nematode that causes unwanted damage to substrates or materials, such as nematodes that attack foodstuffs, seeds, wood, paint, plastic, clothing etc. Examples of such nematodes include, but are not limited to: *Meloidogyne* spp. (e.g., *M. incognita, M. javanica, M. arenaria, M. graminicola, M. chitwoodi* or *M. hapla*); *Heterodera* spp. (e.g., *H. oryzae, H. glycines, H. zeae* or *H. schachtii*); *Globodera* spp. (e.g., *G. pallida* or *G. rostochiensis*); *Ditylenchus* spp. (e.g., *D. dipsaci, D. destructor* or *D. angustus*); *Belonolaimus* spp.; *Rotylenchulus* spp. (e.g., *R. reniformis*); *Pratylenchus* spp. (e.g., *P. coffeae, P. goodeyi* or *P. zeae*); *Radopholus* spp. (e.g., *R. Similis*); *Hirschmaniella* spp. (e.g., *H. oryzae*); *Aphelenchoides* spp. (e.g., *A. besseyi*); *Criconemoides* spp.; *Longidorus* spp.; *Helicotylenchus* spp.; *Hoplolaimus* spp.; *Xiphinema* spp.; *Paratrichodorus* spp. (e.g., *P. minor*); *Tylenchorhynchus* spp;

(5) virus transmitting nematodes (e.g. *Longidorus macrosoma*: transmits *prunus* necrotic ring spot virus, *Xiphinema americanum*: transmits tobacco ring spot virus, *Paratrichadorus teres*: transmits pea early browning virus, or *Trichodorus similis*: transmits tobacco rattle virus).

Specific Nematode Pests Include:

*Dracunculus medinensis*, the roundworm that causes Dracunculiasis (Guinea worm disease); nematodes *Loa* (the African eye worm), *Mansonella streptocerca* and *Onchocerca volvulus*, which cause Cutaneous Filariasis; *Mansonella perstans* and *Mansonella ozzardi*, which cause Body Cavity Filariasis; *Trichinella*, including *T. pseudospiralis* (infecting mammals and birds worldwide), *T. nativa* (infecting Arctic bears), *T. nelsoni* (infecting African predators and scavengers), and *T. britovi* (infecting carnivores of Europe and western Asia), which cause Trichinellosis; *Angiostrongylus cantonensis* (the rat lungworm), which is the most common cause of human eosinophilic meningitis; *Angiostrongylus costaricensis*, which causes abdominal (or intestinal) angiostrongyliasis; *Toxocara*, which causes human toxocariasis; *Gnathostoma spinigerum*, and rarely *G. hispidum*, which cause Gnathostomiasis; and *Anisakis simplex*, or *Pseudoterranova decipiens*, which causes Anisakiasis.

In specific embodiments, the methods and compositions of the subject invention are used to control root-knot nematode (*Meloidogyne incognital*), sting nematode (*Belonolaimus longicaudatus*), soybean cyst nematode (*Heterodera glycines*), lesion nematode (*Pratylenchus sp.*), dagger nematode (*Xiphinema sp.*), and/or citrus nematode (*Tylenchulus semipenetrans*).

Target Plants

Plants that can benefit from application of the products and methods of the subject invention include: Row Crops (e.g., Corn, Soy, Sorghum, Peanuts, Potatoes, etc.), Field Crops (e.g., Alfalfa, Wheat, Grains, etc.), Tree Crops (e.g., Walnuts, Almonds, Pecans, Hazelnuts, Pistachios, etc.), Citrus Crops (e.g., orange, lemon, grapefruit, etc.), Fruit Crops (e.g., apples, pears, etc.), Turf Crops, Ornamentals Crops (e.g., Flowers, vines, etc.), Vegetables (e.g., tomatoes, carrots, etc.), Vine Crops (e.g., Grapes, Strawberries, Blueberries, Blackberries, etc.), Forestry (e.g., pine, spruce, *eucalyptus*, poplar, etc.), Managed Pastures (any mix of plants used to support grazing animals).

The benefit can be in the form of, for example, increased yield, quality, disease and pest resistance, stress reduction (e.g., from salt, drought, heat, etc.) and improved water usage.

Further plants that can benefit from the products and methods of the invention include all plants that belong to the superfamily Viridiplantae, in particular monocotyledonous and dicotyledonous plants including fodder or forage legumes, ornamental plants, food crops, trees or shrubs selected from Acer spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g., *Avena sativa, Avena fatua, Avena byzantina, Avena fatua* var. *sativa, Avena hybrida*), *Averrhoa carambola, Bambusa sp., Benincasa hispida, Bertholletia excelsea, Beta vulgaris, Brassica* spp. (e.g., *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus sp., Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g., *Elaeis guineensis, Elaeis oleifera*), *Eleusine coracana, Eragrostis tef, Erianthus sp., Eriobotrya japonica, Eucalyptus sp., Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g., *Glycine max, Soja hispida* or *Soja max*), *Gossypium hirsutum, Helianthus* spp. (e.g., *Helianthus annuus*), *Hemerocallis fulva, Hibiscus* spp., *Hordeum* spp. (e.g., *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g., *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g., *Oryza sativa, Oryza latifolia*), *Panicum miliaceum, Panicum virgatum, Passiflora edulis, Pastinaca sativa, Pennisetum sp., Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix sp., Sambucus* spp., *Secale cereale, Sesamum* spp., *Sinapis sp., Solanum* spp. (e.g., *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g., *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

Further examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, *sorghum*, wheat, millet, tobacco, etc.), such as corn and soybean plants.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); *zoysia* grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Further plants of interest include *Cannabis* (e.g., *sativa, indica*, and *ruderalis*) and industrial hemp.

Plants of interest include grain plants that provide seeds of interest, oil-seed plants, and leguminous plants. Seeds of interest include grain seeds, such as corn, wheat, barley, rice, *sorghum*, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc.

All plants and plant parts can be treated in accordance with the invention. In this context, plants are understood as meaning all plants and plant populations, such as desired and undesired wild plants or crop plants (including naturally occurring crop plants). Crop plants can be plants that can be obtained by traditional breeding and optimization methods or by biotechnological and recombinant methods, or combinations of these methods, including the transgenic plants and the plant varieties.

Plant parts are understood as meaning all aerial and subterranean parts and organs of the plants such as shoot, leaf, flower and root, examples which may be mentioned being leaves, needles, stalks, stems, flowers, fruit bodies, fruits and seeds, but also roots, tubers and rhizomes. The plant parts also include crop material and vegetative and generative propagation material, for example cuttings, tubers, rhizomes, slips and seeds.

EXAMPLES

It should be understood that the examples and embodiments described herein are for illustrative purposes only and that various modifications or changes in light thereof will be suggested to persons skilled in the art and are to be included within the spirit and purview of this application.

Example 1—Fermentation of *S. bombicola* for Sophorolipid (SLP) Production in a 110 L Distributable Reactor A portable, airlift-type, fully enclosed reactor operated by PLC with water filtration, temperature control unit, and an air blower on board is used. The reactor has a working volume of 90 L when growing *Starmerella bombicola* for SLP production.

In preferred embodiments, the nutrients for SLP production are glucose, urea, yeast extract, canola oil, magnesium sulfate, and potassium phosphate.

The reactor is inoculated with 8 liters of liquid culture grown in flasks. The duration of the cultivation cycle for SLP production is 7-8 days, at 25° C. and pH 3.5, with sampling performed twice a day.

The final concentration of SLP is roughly 10% of working volume, in this case about 9 L of product, containing 300-400 grams of SLP per liter.

Example 2—Fermentation of *S. bombicola* for SLP Production in Portable 14 L Distributable Reactor This reactor is an autoclavable jacketed glass vessel with air spurge and impeller. It is equipped with dissolved oxygen, pH, temperature, and foam prob; it has an integrated control station with a color touchscreen interface, built-in pumps, gas flow controllers, and pH/DO foam/level controllers. The working volume of the reactor is 10 liters.

Nutrient medium contains glucose, yeast extract, urea, and vegetable oil. Inoculum can be a 1 to 2-day old culture of *Starmerella bombicola* at about 5-10% of the total culture volume. Cultivation duration and readymade product collection continues for 5-14 days. Final sophorolipid production can reach 1-2 kilogram per cycle.

Example 3—Fermentation of *Wickerhamomyces* and/or *Pichia* Yeast for SLP Production in a 450 L Distributable Reactor A movable airlift reactor operated by PLC with water filtration, temperature control unit, and air blower for sufficient aeration is used. The process can be carried out as batch cultivation process. The reactor has a working volume of 400 L when growing *Wickerhamomyces* or *Pichia* for SLP production.

In preferred embodiments, the nutrients for SLP production are glucose, urea, yeast extract, canola oil, magnesium sulfate, and potassium phosphate.

Inoculation of this reactor requires up to 5% liquid seed culture of working volume. The duration of the cultivation cycle is 7 days, at a temperature 25° C. and pH 3.5, with sampling performed twice a day.

The final concentration of SLP is roughly 20-25% of the working volume, in this case greater than 90 L of product forms.

Example 4—Fermentation of *Wickerhamomyces* and/or *Pichia* Yeast for Cell and Single Cell Protein Production in 900 L Distributable Reactor A portable reactor divided into two tanks run by a central airlift to help mix the two tanks simultaneously is used. The reactor has a working volume of 600 L when growing *Wickerhamomyces* and/or *Pichia* for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach 90 kilos per cycle with protein concentration up to 45 kilos.

Example 5—Fermentation of *Wickerhamomyces* and/or *Pichia* Yeast for Cell and Single Cell Protein Production in 2000 L Distributable Reactor A portable reactor divided into two square tanks accompanied with 2 loops for mass exchange between them is used. The reactor has a working volume of 2000 L when growing *Wickerhamomyces* and/or *Pichia* for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach up to 200 kilos per cycle with protein concentration up to 100 kilos.

Example 6—Fermentation of *Pseudozyma aphidis* for Mannosylerythritol Lipid (MEL) Production in Portable 14 L Distributable Reactor This is a steam autoclavable jacketed glass vessel with air spurge and Rushton impeller. It is equipped with DO, pH, temperature, and foam probe. It has an integrated control station with a color touchscreen interface, built-in pumps, gas flow controllers, and pH/DO foam/level controllers. The working volume of the reactor is 10 liters.

Nutrient medium composition: Sodium nitrate, Potassium phosphate, Magnesium sulfate, yeast extract, and vegetable oil. Inoculum can be a 1 to 2 day old culture of *Pseudozyma aphidis*, at about 5-10% of the total culture volume. Cultivation duration and sample collection: 9-15 days. Final MEL production: 800-1000 grams.

Example 7—Use of SLP to Reduce Root-Knot Nematode Eggs on Tomato Plants

*Starmerella bombicola* was grown as described above. At the end of the fermentation culture, broth settles and most of the SLP separates as a dark brown layer (concentration of about 500 gm/L). This brown layer primarily contains SLP and some cells as well. The layer is collected and the pH is adjusted to pH 7.0. That solution is then diluted with water to achieve the desired concentrations.

Day 1 Germinate tomato (Moneymaker) seeds
Day 14 Prepare sand/turface (1:1) with 1% fertilizer (osmocote), transplant tomato 2-week seedlings
Day 28 Inoculate microbes by soil drench to 4-week old plants. For each 10 cm×10 cm square pot, 80-100 ml culture was enough to wet the soil.
Day 32 Four days later after the inoculation of microbes, apply RKN eggs (4000 eggs per pot) to each plant.
Day 76 Six weeks after the inoculation of eggs, harvest the plants.

After harvesting, the plants were washed under tap water to remove the sand/turface attached on the root. the fresh weight of roots were recorded. Subsequently, the roots were cut into small pieces and put in a small plastic lunch bag. After 200 ml 5% bleach was added, the bag was incubated and shaken gently for 15 min. Then the eggs were counted in 10 ul samples in triplicate under Stereo Microscope. The total number of eggs on each root was calculated. Finally, the number of eggs in each gram of root biomass was calculated.

SLP 0.25% also shows activity against Root Knot Nematode (RNK) with a reduction of eggs by about 52%.

Example 8—Comparison of SLP, MEL, and Nimitz® in Ability to Control Root-Knot, Sting, and Lesion Nematodes Nimitz® is the first new chemical nematicide to be developed in more than 20 years. Nimitz® causes irreversible and rapid nematicidal activity immediately following an application. Within one hour of contact, nematodes cease feeding and quickly become paralyzed. Within 24 to 48 hours, pest mortality occurs rather than temporary nematostatic (immobilizing) activity, as seen with organophosphate and carbamate nematicides.

*Pseudozyma aphidis* was grown as described above. At the end of fermentation the whole culture broth was used, as MEL is very hard to separate without using any solvent. MEL is then diluted with water to the desired concentrations immediately prior to application.

*Starmerella bombicola* was grown as described above. At the end of the fermentation culture, broth settles and most of the SLP separates as a dark brown layer (concentration of about 500 gm/L). This brown layer primarily contains SLP and some cells as well. The layer is collected and the pH is adjusted to pH 7.0. That solution is then diluted with water to achieve the desired concentrations.

The following bioassay was conducted: Fill glass cavity slides with appropriate amounts of test product. Add known population of target nematode juveniles to the solution containing nematicide. Maintain the cavity slides at room temperature. Nematode mortality can be judged by counting the number of nematodes at 24, 48 and 72 hours. Percentage mortality was calculated as: [mean of dead number of juveniles in treatment/total number of juveniles in treatment]×100.

A. Root-Knot Nematode

Figure 2:
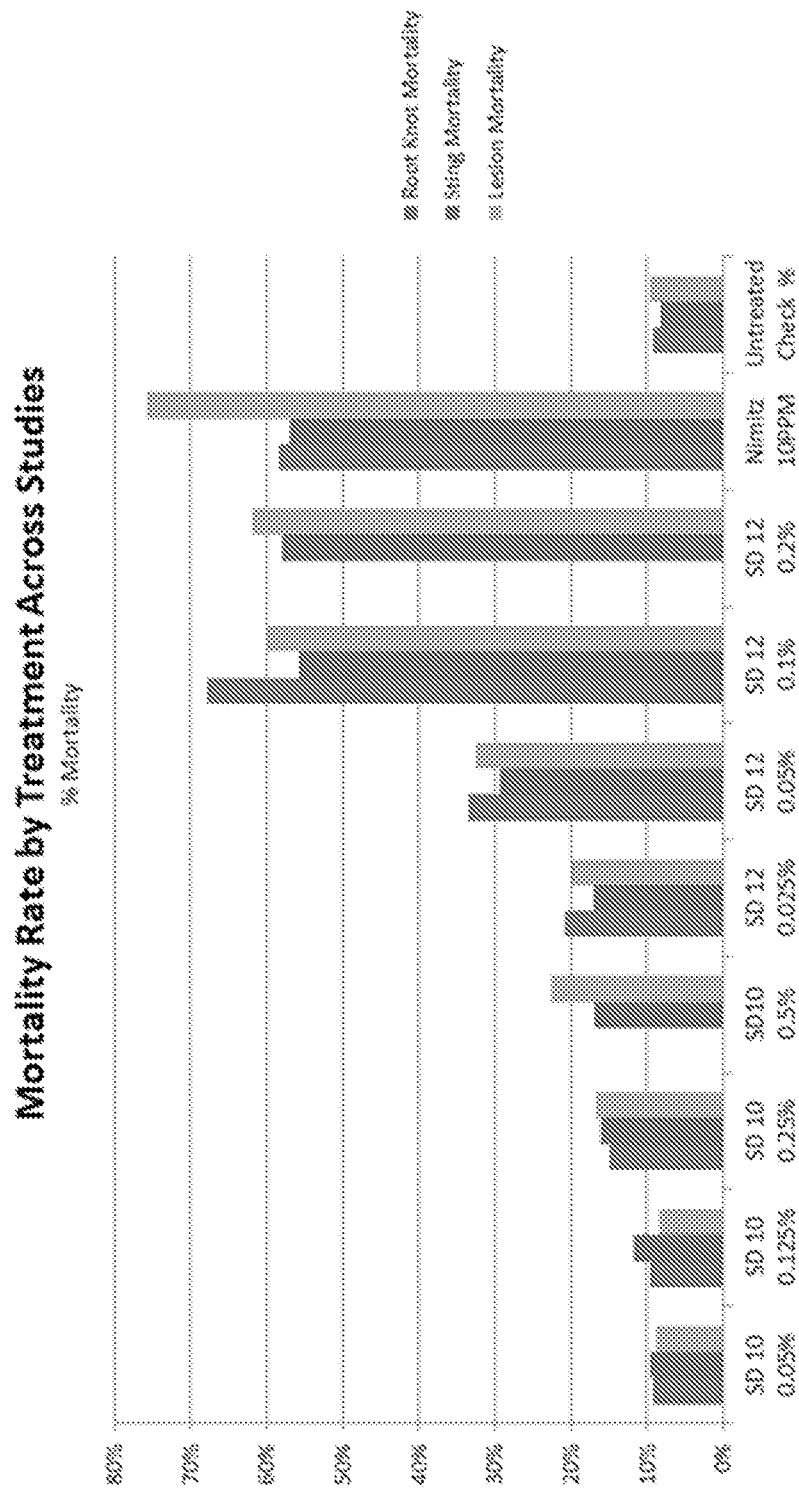
FIG. 2 shows nematode mortality rate after 3 days of treatment under various conditions: SD10 at 0.05% (v/v), 0.125% (v/v), 0.25% (v/v), and 0.5% (v/v), respectively; SD12 at 0.025% (v/v), 0.05% (v/v), 0.1% (v/v), and 0.2% (v/v), respectively; Nimitz® at 10 ppm ai; and untreated check.

The Root-knot nematode (*Meloidogyne incognita*) mortality (i.e., how many of the nematodes were killed) and lack of motility (i.e., how many of the nematodes were deathly ill) were determined after 3 days of treatment of SLP (SD10) or MEL (SD12) at various concentrations and compared with the treatment of Nimitz® and untreated control (FIGS. 1 and 2). The percent mortality was calculated by the number of dead nematode/the number of total counts of nematode before the test. The percent non-motile nematodes was calculated by the number of non-motile nematodes/the number of live nematodes. Thus, motility is calculated as the percentage of those nematodes that were not killed but are determined to be non-motile.

The high level of MELs (0.1% v/v) was the most effective treatment in the test. It was significantly more effective than Nimitz® with respect to mortality. A clear dose response was observed. The results also show that SLP was as effective as Nimitz® on the root knot nematode mortality and lack of motility.

B. Sting Nematode

The sting nematode (*Belonolaimus longicaudatus*) mortality and motility reduction rates were determined after 3 days of treatment of SLP or MEL at various concentrations and compared with the treatment of Nimitz® and untreated control (FIGS. 1 and 2).

The results show that both SLP and MEL increase the sting nematode mortality and motility reduction rate in a dose dependent manner. The high levels of MEL (0.1% or 0.2% v/v) were the most effective treatment in the test. They were as effective as Nimitz® with respect to mortality and more effective than Nimitz® with respect to the motility reduction rate.

C. Lesion Nematode

The lesion nematode (*Pratylenchus sp.*) mortality and motility reduction rates were determined after 3 days of treatment of SLP or MEL at various concentrations and compared with the treatment of Nimitz® and untreated control (FIGS. 1 and 2).

The results show that both SLP and MEL increase the lesion nematode mortality and motility reduction rate in a dose dependent manner. MEL was more effective than SLP and comparable to Nimitz® in the test.

Example 9—Evaluation of Varying Treatments Against Southern Root Knot Nematodes in Pathology Lab Jar Tests SLP treatment (SD10) and MEL treatment (SD12) applied directly to nematode-infected soil were tested at two rates, alone or together, and compared to Nimitz® and untreated control for decreasing living Southern Root Knot Nematode populations. Counts were taken at three different time points after treatment.

Six replicates of 7 treatments were conducted in glass jars containing 350 cm$^3$ of 99% sandy soil. The jars were inoculated with 70 adult Southern Root Knot nematodes (*Meloidogyne incognita*). One application of treatment was made just after nematode inoculation, where 85 mL of treatment was hand poured into each jar. Treatment mixtures were prepared according to Table 1 (below). Living and dead nematode counts were made at day 3, day 14, and day 23 post-treatment. Counts of non-motile nematodes, as a percentage of the total living, were also tabulated.

TABLE 1

Preparation of Treatment Mixtures

| Trt No. | Treatment Name | Form Type | Rate | Rate Unit | Amount of Product to Measure/ |
|---|---|---|---|---|---|
| 1 | SD10 | L | 0.25 | % v/v | 2.5 ml/mx |
| 2 | SD10 | L | 0.5 | % v/v | 4.999 ml/mx |
| 3 | SD12 | L | 0.1 | % v/v | 0.9999 ml/mx |
| 4 | SD12 | L | 0.2 | % v/v | 2.0 ml/mx |
| 5 | SD10 + SD12 | L | 0.25 | % v/v | 2.5 ml/mx |
|   |   | L | 0.1 | % v/v | 0.9999 ml/mx |
| 6 | Nimitz ® | L | 10 | ppm pr | 9.999 ul/mx |
| 7 | Untreated Check |   |   |   |   |

Reps: 6; Spray volume: 85 mL/item; Plots; 4 × 20 ft.; Mix size: 1 L (0 L calculated mix size).

Results

Jar test results for SD10 and SD12 products suggest a positive dose response for activity against Southern Root Knot Nematodes. SD10 and SD12 applied together at a low rate were not as effective as either product alone at a higher rate. Nimitz® provided superior control.

Figure 3:
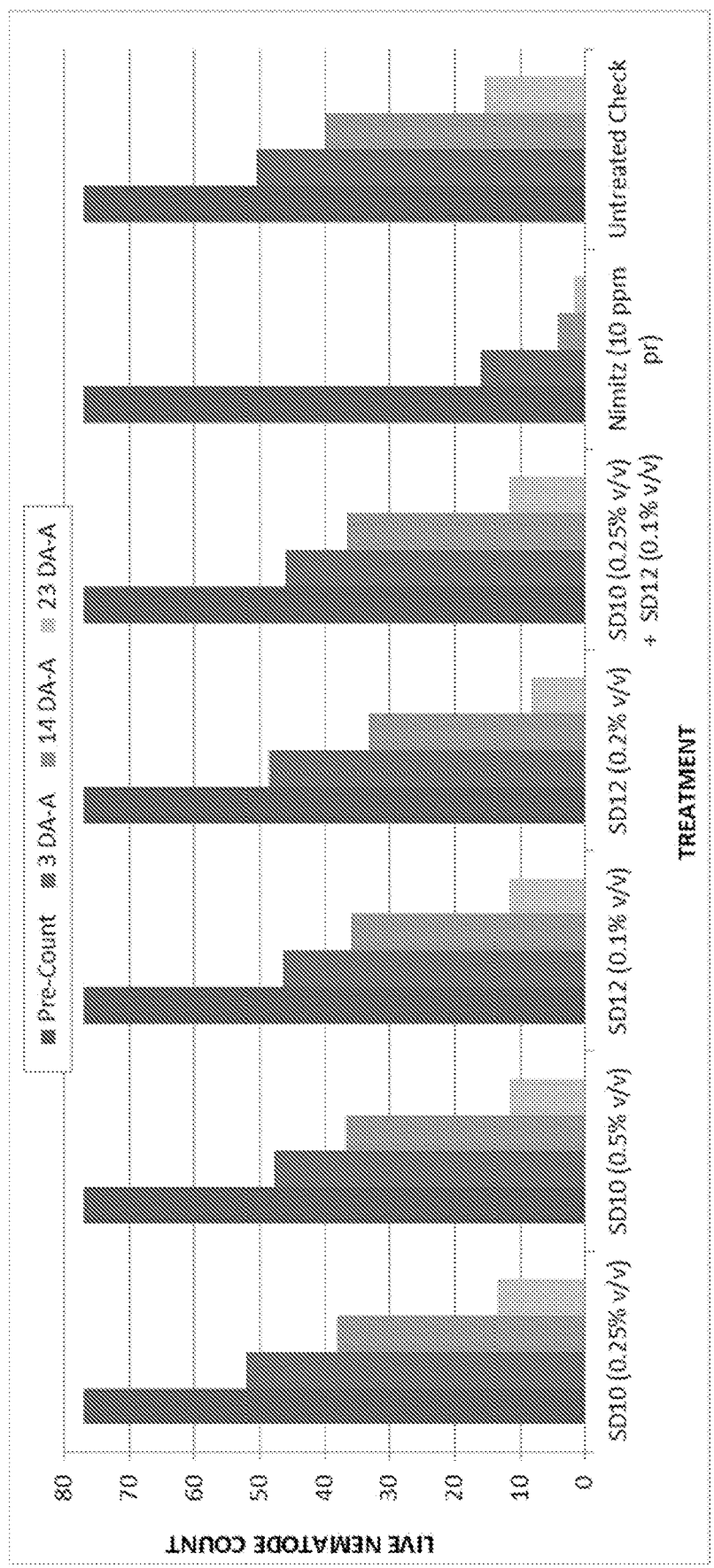
FIG. 3 shows live nematode count after 3, 14, and 23 days of various soil treatments in pathology lab jar tests: SD10 at 0.25% (v/v) and 0.5% (v/v); SD12 at 0.1% (v/v) and 0.2% (v/v); SD10 (0.25% v/v/)+SD12 (0.1% v/v); Nimitz® at 10 ppm pr; and untreated check.
Figure 4:
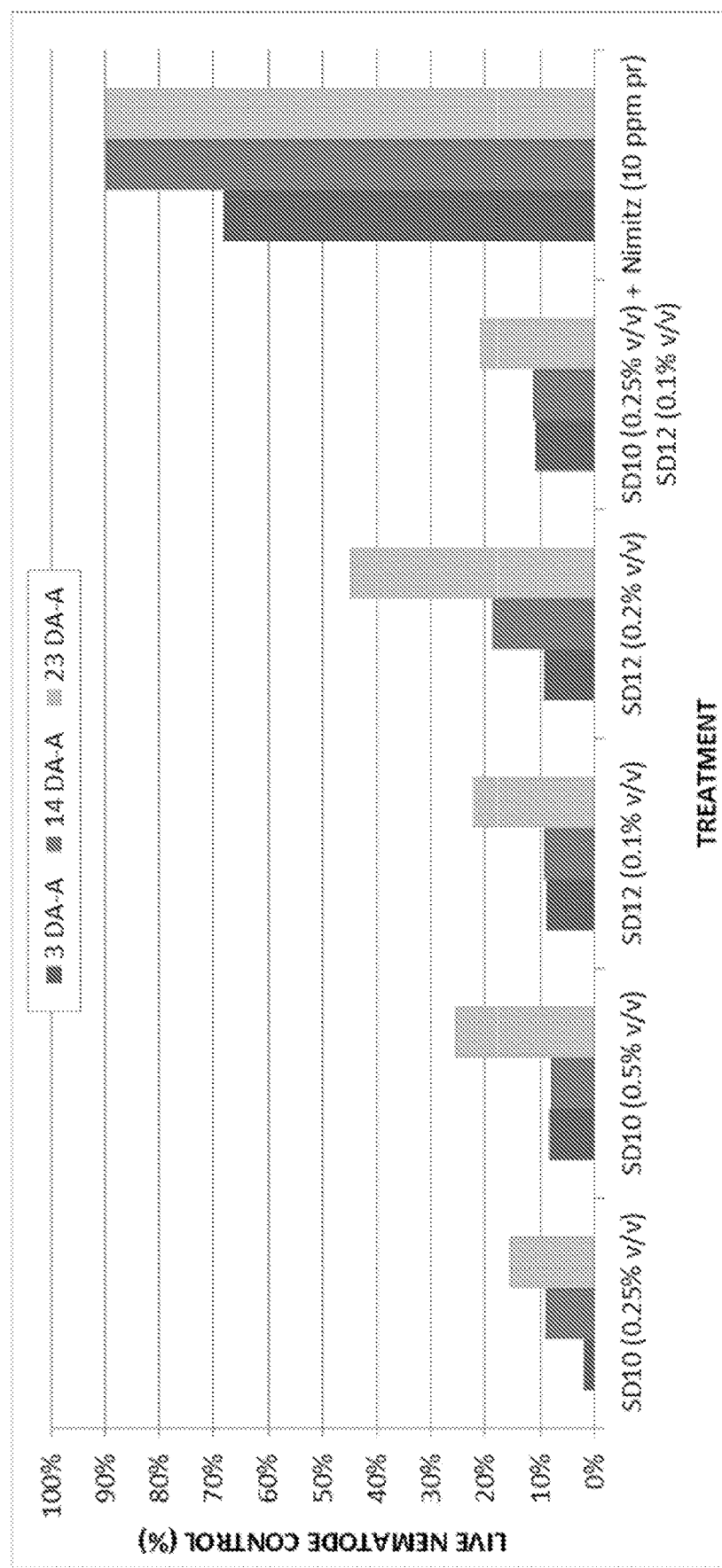
FIG. 4 shows live nematode control (i.e., nematode death) after 3, 14, and 23 days of various soil treatments in pathology lab jar tests: SD10 at 0.25% (v/v) and 0.5% (v/v); SD12 at 0.1% (v/v) and 0.2% (v/v); SD10 (0.25% v/v/)+SD12 (0.1% v/v); Nimitz® at 10 ppm pr; and untreated check.

FIG. 3 and Table 2 (below) show live nematode counts for each treatment. FIG. 4 and Table 3 (below) show live nematode control (i.e., nematode death rate) for each treatment.

TABLE 2

Live Nematode Count

| Trt No. | Treatment Name | Rate | Rate Unit | Appl Code | Pre-Count | | 3 DA-A | | 14 DA-A | | 23 DA-A | |
|---|---|---|---|---|---|---|---|---|---|---|---|---|
| 1 | SD10 | 0.25 | % v/v | A | 77.00 | a | 52.00 | a | 38.17 | a | 13.50 | ab |
| 2 | SD10 | 0.5 | % v/v | A | 77.00 | a | 47.67 | a | 36.67 | a | 11.50 | b |
| 3 | SD12 | 0.1 | % v/v | A | 77.00 | a | 46.33 | a | 36.00 | a | 11.83 | b |
| 4 | SD12 | 0.2 | % v/v | A | 77.00 | a | 48.50 | a | 33.33 | a | 8.17 | c |

TABLE 2-continued

| | | | | Live Nematode Count | | | | | | | |
|---|---|---|---|---|---|---|---|---|---|---|---|
| Trt No. | Treatment Name | Rate | Rate Unit | Appl Code | Pre-Count | | 3 DA-A | | 14 DA-A | | 23 DA-A | |
| 5 | SD10 + SD12 | 0.25 0.1 | % v/v % v/v | A A | 77.00 | a | 46.00 | a | 36.50 | a | 11.83 | b |
| 6 | Nimitz® | 10 | ppm pr | A | 77.00 | a | 16.00 | b | 4.17 | b | 1.67 | d |
| 7 | Untreated Check | | | | 77.00 | a | 50.50 | a | 39.83 | a | 15.33 | a |

There was significantly higher control recorded as early as day 3 (3 DA-A) in the jars treated with Nimitz® (10 ppm). For both SD10 and SD12, there were significant dose responses observed for each at 23 DA-A, with the higher-rate treated samples having lower nematode counts than the lower-rate samples. When both SD10 and SD12 were applied at the low rate in combination, nematode mortality was not significantly boosted to levels seen in higher-rate treatments.

TABLE 3

| | | | | Live Nematode Control (%) | | | | | | |
|---|---|---|---|---|---|---|---|---|---|---|
| Trt No. | Treatment Name | Rate | Rate Unit | Appl Code | 3 DA-A | | 14 DA-A | | 23 DA-A | |
| 1 | SD10 | 0.25 | % v/v | A | 1.84 | bc | 9.09% | bc | 15.56 | cd |
| 2 | SD10 | 0.5 | % v/v | A | 8.29 | bc | 8.03% | bc | 25.72 | c |
| 3 | SD12 | 0.1 | % v/v | A | 8.84 | bc | 9.24% | bc | 22.18 | c |
| 4 | SD12 | 0.2 | % v/v | A | 9.39 | b | 18.64% | b | 44.88 | b |
| 5 | SD10 + SD12 | 0.25 0.1 | % v/v % v/v | A A | 10.88 | b | 11.40% | bc | 20.90 | c |
| 6 | Nimitz® | 10 | ppm pr | A | 68.24 | a | 89.94% | a | 89.77 | a |
| 7 | Untreated Check | | | | 0.00 | c | 0.00% | c | 0.00 | d |

Figure 5:
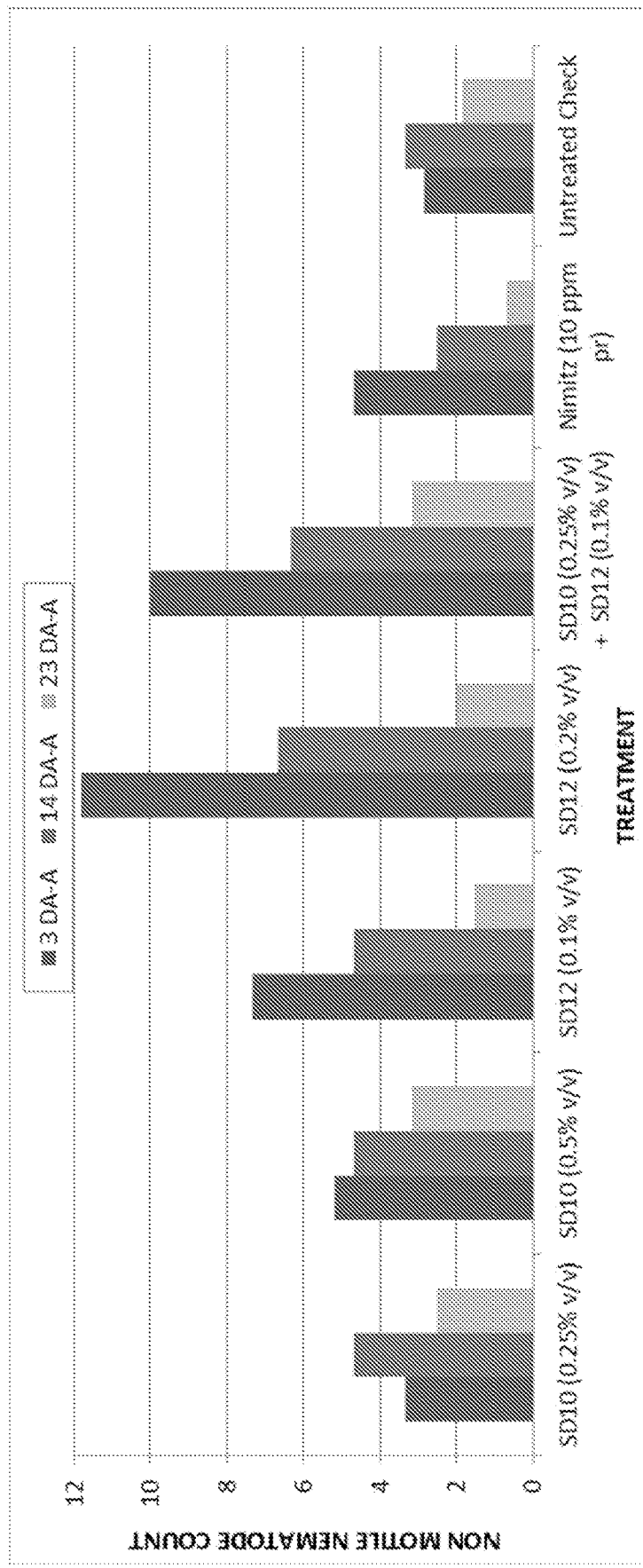
FIG. 5 shows non-motile nematode count after 3, 14, and 23 days of various soil treatments in pathology lab jar tests: SD10 at 0.25% (v/v) and 0.5% (v/v); SD12 at 0.1% (v/v) and 0.2% (v/v); SD10 (0.25% v/v/)+SD12 (0.1% v/v); Nimitz® at 10 ppm pr; and untreated check.
Figure 6:
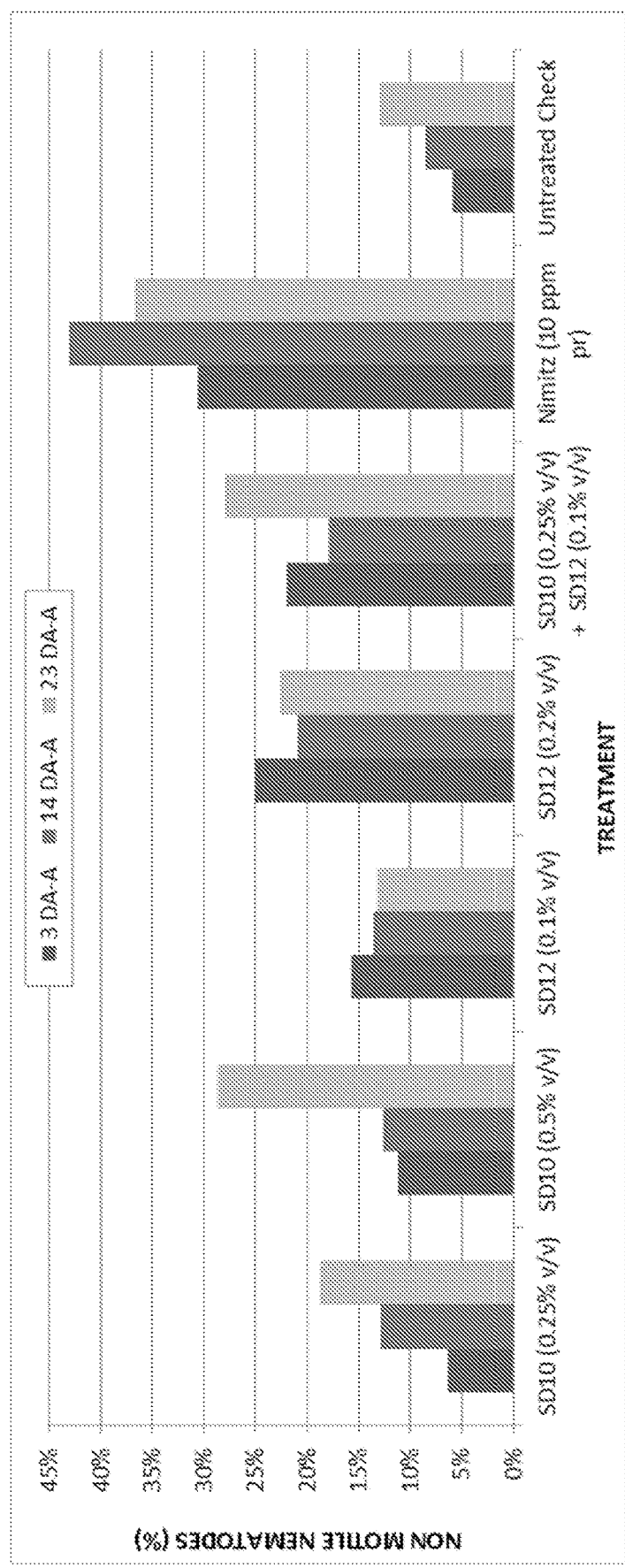
FIG. 6 shows non-motile living nematode count after 3, 14, and 23 days of various soil treatments in pathology lab jar tests: SD10 at 0.25% (v/v) and 0.5% (v/v); SD12 at 0.1% (v/v) and 0.2% (v/v); SD10 (0.25% v/v/)+SD12 (0.1% v/v); Nimitz® at 10 ppm pr; and untreated check.

FIG. 5 and Table 4 (below) show non-motile nematode counts. FIG. 6 and Table 5 (below) show non-motile living nematode count (%).

TABLE 4

| | | | | Non Motile Nematode Count | | | | | | |
|---|---|---|---|---|---|---|---|---|---|---|
| Trt No. | Treatment Name | Rate | Rate Unit | Appl Code | 3 DA-A | | 14 DA-A | | 23 DA-A | |
| 1 | SD10 | 0.25 | % v/v | A | 3.33 | c | 4.67 | bc | 2.50 | ab |
| 2 | SD10 | 0.5 | % v/v | A | 5.17 | bc | 4.67 | bc | 3.17 | a |
| 3 | SD12 | 0.1 | % v/v | A | 7.33 | b | 4.67 | bc | 1.50 | bc |
| 4 | SD12 | 0.2 | % v/v | A | 11.83 | a | 6.67 | a | 2.00 | abc |
| 5 | SD10 + SD12 | 0.25 0.1 | % v/v % v/v | A A | 10.00 | a | 6.33 | ab | 3.17 | a |
| 6 | Nimitz® | 10 | ppm pr | A | 4.67 | c | 2.50 | d | 0.67 | c |
| 7 | Untreated Check | | | | 2.83 | c | 3.33 | cd | 1.83 | abc |

Non-motile nematode counts were lowest in the Nimitz®-treated samples. At 3 DA-A there was a higher percentage of non-motile nematodes as rates of either SD10 or SD12 increased, suggesting early activity of the pesticides did not result in immediate fatality. By 14 DA-A the percentage of living nematodes rated non-motile were no different statistically, among the SD-treated jars.

TABLE 5

| | | | | Non Motile Living Nematode Count (%) | | | | | |
|---|---|---|---|---|---|---|---|---|---|
| Trt No. | Treatment Name | Rate | Rate Unit | Appl Code | 3 DA-A | | 14 DA-A | | 23 DA-A | |
| 1 | SD10 | 0.25 | % v/v | A | 6.39 | e | 12.86 | b | 18.80 | a |
| 2 | SD10 | 0.5 | % v/v | A | 11.18 | de | 12.55 | b | 28.61 | a |
| 3 | SD12 | 0.1 | % v/v | A | 15.78 | cd | 13.51 | b | 13.16 | a |
| 4 | SD12 | 0.2 | % v/v | A | 25.03 | ab | 20.85 | b | 22.59 | a |
| 5 | SD10 + SD12 | 0.25 0.1 | % v/v % v/v | A A | 22.00 | bc | 17.89 | b | 27.85 | a |
| 6 | Nimitz ® | 10 | ppm pr | A | 30.55 | a | 43.06 | a | 36.67 | a |
| 7 | Untreated Check | | | | 5.91 | e | 8.54 | b | 13.01 | a |

Example 10—Use of MEL as a Nematicide in a Cucumber Plant Micro-Plot System

An outdoor microplot located in Thonotosassa, Fla., USA, was used to study MEL nematode treatment for cucumber plants compared to Nimitz® and an untreated control. Six different treatment groups, each consisting of 8 plants, were studied. For groups receiving SD12 (0.2% ai/v) treatment, treatment was applied to soil once, twice or three times. Both nematode count and galling rate were collected at harvest. Plant vigor, yield and weight of plants were also measured.

Plants receiving Nimitz® (5 pt/a) treatment were planted in soil treated 7 days before planting (chemical treatment is too phytotoxic to be applied in growing season). For all plants receiving SD12 treatment, the first application of SD12 to soil (60 mL for each plant) occurred at the time of planting. For plants receiving SD12 double treatment and triple treatment, the second 60 mL application occurred two weeks after the first treatment. For plants receiving SD12 triple treatment, the third 60 mL application occurred four weeks after the first treatment.

Nematode counts and galling rates were collected for all groups 31 days after the final SD12 treatment in the triple treatment group. Plant vigor (0-10 index/scale), yield (lbs.) and weight (lbs.) were measured the following day.

Results

Figure 7:
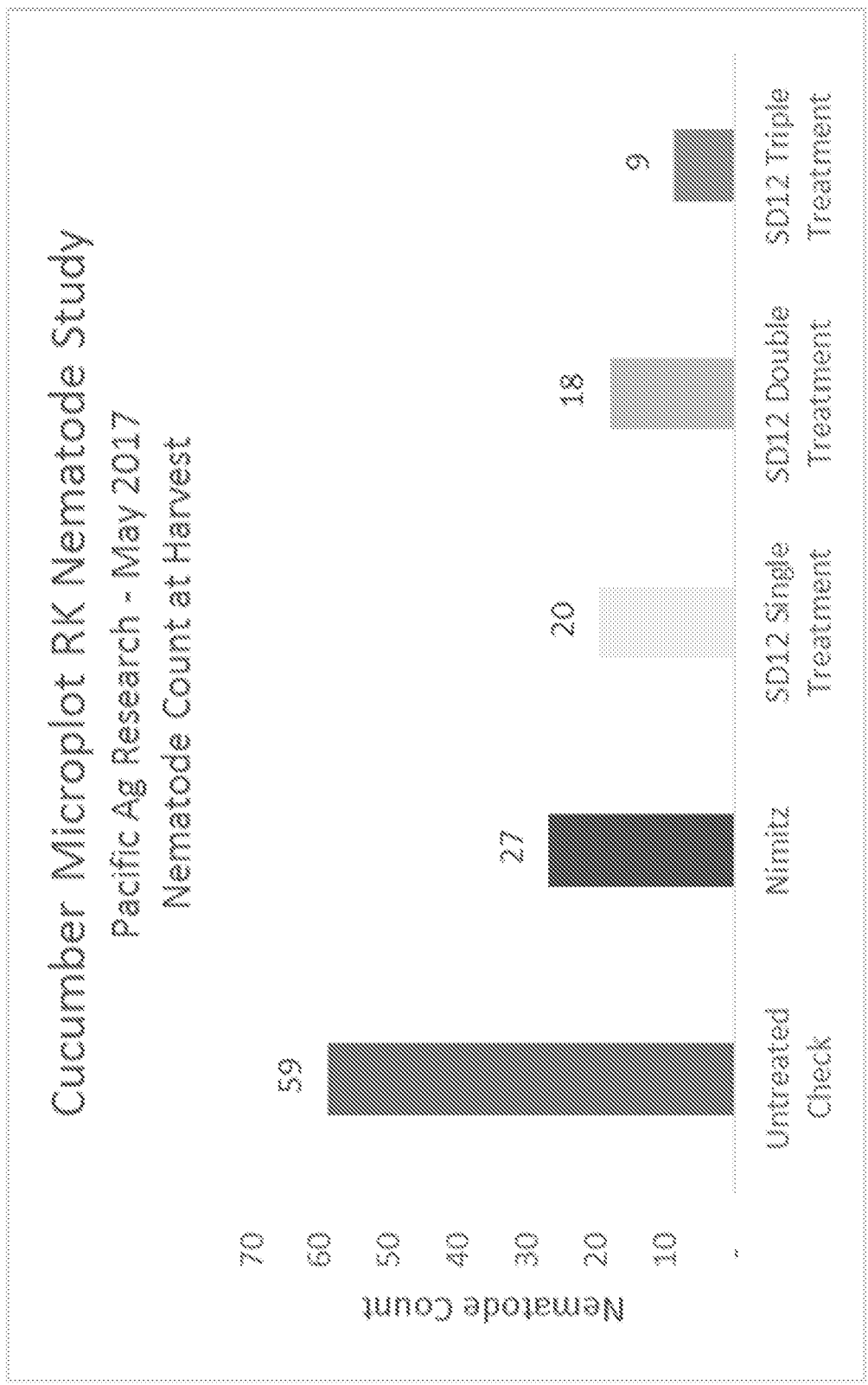
FIG. 7 shows gall formation rate at harvest for a cucumber microplot treated with 5 different treatments: untreated check; Nimitz® at 5 pt/a; SD12 0.2% (ai/v) single treatment; SD12 0.2% (ai/v) double treatment; SD12 0.2% (ai/v) triple treatment.
Figure 8:
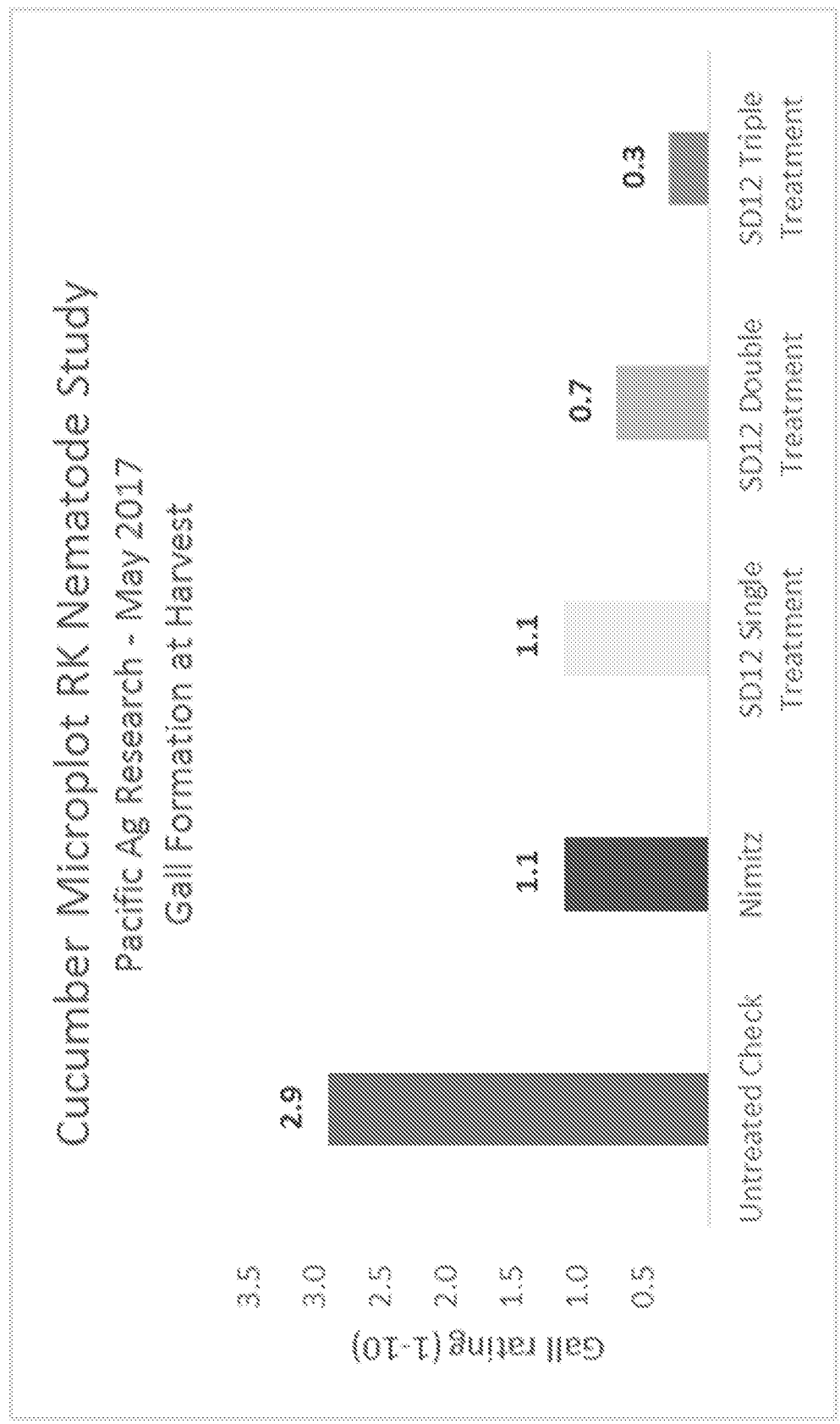
FIG. 8 shows nematode count at harvest for a cucumber microplot treated with 5 different treatments: untreated check; Nimitz® at 5 pt/a; SD12 0.2% (ai/v) single treatment; SD12 0.2% (ai/v) double treatment; SD12 0.2% (ai/v) triple treatment.

A rate response was observed in galling (FIG. 7 and Table 6 (below)) and in post-treatment nematode counts (FIG. 8 and Table 7 (below)). SD12 performed to commercial standards. There was no significant separation between SD12 treatments and the Nimitz® treatment, but significant differences were observed between SD12 treatments and the untreated check. Plant vigor, yield and weight at harvest are reported in Table 8 below.

TABLE 6

| | | Galling Rate (1-10 index/scale) | | | | |
|---|---|---|---|---|---|---|
| Trt No. | Treatment Name | Rate | Rate Unit | Appl Code | Gall Rate | |
| 1 | Untreated | | | | 2.9 | a |
| 2 | Nimitz ® | 5 | pt/a | A | 1.1 | b |
| 3 | SD12 × 1 | 0.2 | % ai/v | B | 1.1 | b |
| 4 | SD12 × 2 | 0.2 | % ai/v | BC | 0.7 | b |
| 5 | SD12 × 3 | 0.2 | % ai/v | BCD | 0.3 | b |

LSD (P = .05) = 0.88;
SD = 0.86;
CV = 69.39;
Bartlett's X2 = 11.754;
P (Bartlett's X2) = 0.019*;
Replicate F = 3.712;
Replicate Prob(F) = 0.0061;
Treatment F = 11.133;
Treatment Prob(F) = 0.0001.

TABLE 7

| | | Nematode Count | | | | |
|---|---|---|---|---|---|---|
| Trt No. | Treatment Name | Rate | Rate Unit | Appl Code | Nematode Count | |
| 1 | Untreated | | | | 59 | a |
| 2 | Nimitz ® | 5 | pt/a | A | 27 | b |
| 3 | SD12 × 1 | 0.2 | % ai/v | B | 20 | b |
| 4 | SD12 × 2 | 0.2 | % ai/v | BC | 18 | b |
| 5 | SD12 × 3 | 0.2 | % ai/v | BCD | 9 | b |

LSD (P = .05) = 17.33;
SD = 16.3;
CV = 63.88;
Bartlett's X2 = 17.263;
P (Bartlett's X2) = 0.002*;
Replicate F = 2.774;
Replicate Prob(F) = 0.0261;
Treatment F = 10.44;
Treatment Prob(F) = 0.0001.

TABLE 8

| Plant vigor (0-10), yield (lbs.) and weight (lbs.) measurements at plant harvest. | | | | | | | | | | |
|---|---|---|---|---|---|---|---|---|---|---|
| Trt No. | Treatment Name | Rate | Rate Unit | Appl Code | Vigor | | Yield | | Weight | |
| 1 | Untreated | | | | 6.2 | b | 2.188 | a | 1.131 | a |
| 2 | Nimitz ® | 5 | pt/a | A | 8.0 | a | 3.063 | a | 1.550 | a |
| 3 | SD12 × 1 | 0.2 | % ai/v | B | 8.1 | a | 2.438 | a | 1.288 | a |
| 4 | SD12 × 2 | 0.2 | % ai/v | BC | 8.4 | a | 2.638 | a | 1.263 | a |
| 5 | SD12 × 3 | 0.2 | % ai/v | BCD | 8.2 | a | 3.281 | a | 1.425 | a |

Example 11—Evaluation of Nematode Attractant Efficacy

Counts and infestation percentages of Southern Root Knot Nematodes were taken in four 11.6 in.×7.6 in. sealed chambers containing lake fine sand soil spiked with an attractant material. Pre-made, purchased Valerian root extract was blended with water, vegetable glycerin and 20% grain alcohol to produce the attractant.

Figure 9:
FIG. 9 shows a plot set-up for evaluation of nematode attractant efficacy, including locations of nematode inoculation zone and attractant application zone.

Each plot was inoculated with nematodes in a 2 cm diameter zone. 10 ml, of the nematode attractant was added in a 3 cm (h)×1 cm (w) zone, 2 cm from the inoculation zone (FIG. 9).

Nematode counts and infestation percentages were taken in three locations, 3 days after treatment and 8 days after treatment. The three locations tested included the center of the inoculation zone, the attractant zone, and the untreated area.

Results

Figure 10:
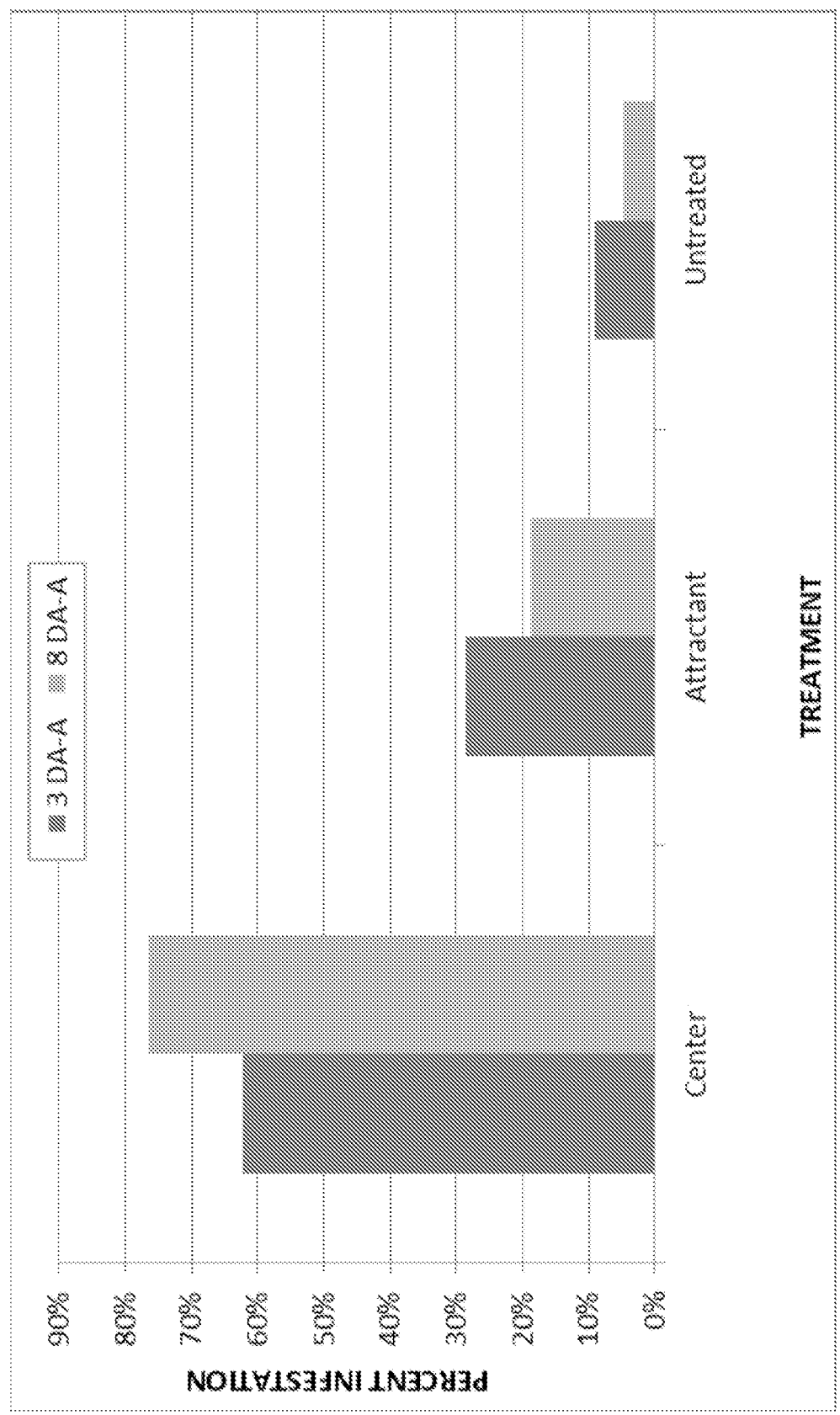
FIG. 10 shows percent infestation (of total plot nematode population) at three different locations in plots for nematode attractant evaluation. "Center" refers to center of inoculation zone, "attractant" refers to the attractant zone, and "untreated" refers to all other plot areas.

Results are summarized in FIG. 10 and in Table 9 (below). The migrations towards the attractant or untreated area was significantly different relative to the inoculation area as a percentage of total population. At 24 and 48 hour sampling events, there were more nematodes counted in the attractant zone than the untreated areas of the chamber by more than 14%; however, the central zone where the nematodes were inoculated held the most nematodes overall.

TABLE 9

Nematode Count and Infestation Percentage in Attractant Evaluation

| Trt No. | Treatment Zone | Rate | Rate Unit | Count 3 DA-A | Count 8 DA-A | Infest % 3 DA-A | Infest % 8 DA-A |
|---|---|---|---|---|---|---|---|
| 1 | Center | | | 63.50 a | 22.50 a | 62.17 a | 76.52 a |
| 2 | Treated—Attractant | 10 | mL/item | 27.50 b | 6.00 b | 28.67 b | 18.66 b |
| 3 | Untreated | | | 8.75 b | 1.75 b | 9.16 c | 4.82 c |

All patents, patent applications, provisional applications, and publications referred to or cited herein are incorporated by reference in their entirety, including all figures and tables, to the extent they are not inconsistent with the explicit teachings of this specification.

The description herein of any aspect or embodiment of the invention using terms such as "comprising," "having," "including" or "containing" with reference to an element or elements is intended to provide support for a similar aspect or embodiment of the invention that "consists of," "consists essentially of," or "substantially comprises" that particular element or elements, unless otherwise stated or clearly contradicted by context.

The invention claimed is:

1. A method for controlling nematodes wherein said method comprises preparing a nematicidal composition by cultivating a *Pseudozyma aphidis* microorganism wherein the *Pseudozyma aphidis* microorganism produces a mannosylerythritol lipid (MEL) biosurfactant; cultivating a *Starmerella bombicola* microorganism wherein the *Starmerella bombicola* microorganism produces a sophorolipid (SLP) biosurfactant; and mixing the cultivated *Pseudozyma aphidis* and MEL with the cultivated *Starmerella bombicola* and SLP, wherein said nematicidal composition comprises the *Pseudozyma aphidis* microorganism, the MEL, a broth in which the *Pseudozyma aphidis* microorganism was cultivated, as well as the *Starmerella bombicola* microorganism, the SLP, and a broth in which the *Starmerella bombicola* microorganism was cultivated, and wherein said method further comprises applying the nematicidal composition to nematodes and/or their environment.

2. The method, according to claim 1, used to control one or more of the following nematodes: *Meloidogyne incognital, Meloidogyne hapla, Meloidogyne arenaria, Meloidogyne incognita, Belonolaimus longicaudatus, Heterodera glycines, Pratylenchus sp., Xiphinema sp.*, and *Tylenchulus semipenetrans*.

3. The method, according to claim 1, wherein said method is used to control a nematode pest of a plant.

4. The method, according to claim 3, wherein the plant is selected from tomatoes, soybeans, corn, *citrus* and turfgrasses.

5. The method, according to claim 3, wherein the composition is applied as a seed treatment.

6. The method according to claim 1, wherein the composition is applied to soil.

7. A method for controlling nematodes wherein said method comprises applying to the nematodes, and/or to an environment of the nematodes, a composition consisting essentially of: a Pseudozyma aphids microorganism and a broth in which it was grown, wherein said broth comprises a mannosylerythritol lipid (MEL); and a *Starmerella bombicola* microorganism and a broth in which it was grown, wherein said *Starmerella bombicola* broth comprises a sophorolipid (SLP).

8. The method, according to claim 7, used to control a nematode selected from root-knot nematode, sting nematode, soybean cyst nematode, lesion nematode, dagger nematode, and *citrus* nematode.

* * * * *